(12) United States Patent
Alipour et al.

(10) Patent No.: US 10,351,886 B2
(45) Date of Patent: *Jul. 16, 2019

(54) METHODS FOR HIGH YIELD PRODUCTION OF FURANS FROM BIOMASS SUGARS AT MILD OPERATING CONDITIONS

(71) Applicant: The University of Toledo, Toledo, OH (US)

(72) Inventors: Siamak Alipour, Toledo, OH (US); Bin Li, Toledo, OH (US); Sasidhar Varanasi, Toledo, OH (US); Patricia Relue, Toledo, OH (US); Sridhar Viamajala, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/823,232

(22) Filed: Nov. 27, 2017

(65) Prior Publication Data

US 2018/0127793 A1     May 10, 2018

Related U.S. Application Data

(62) Division of application No. 15/033,376, filed as application No. PCT/US2014/063661 on Nov. 3, 2014, now Pat. No. 9,828,615.

(60) Provisional application No. 61/898,889, filed on Nov. 1, 2013.

(51) Int. Cl.
*C12P 17/04* (2006.01)
*C07D 307/50* (2006.01)

(52) U.S. Cl.
CPC ............ *C12P 17/04* (2013.01); *C07D 307/50* (2013.01)

(58) Field of Classification Search
None
See application file for complete search history.

(56) References Cited

U.S. PATENT DOCUMENTS

2009/0234146 A1*   9/2009   Cooney .............. B01D 11/0288
                                                  554/174
2013/0074397 A1*   3/2013   Varanasi .................. C07H 1/08
                                                    44/313

FOREIGN PATENT DOCUMENTS

WO    WO2013/047984    *   4/2013
WO    WO2013/079819    *   6/2013

* cited by examiner

*Primary Examiner* — Hope A Robinson
(74) *Attorney, Agent, or Firm* — MacMillan, Sobanski & Todd, LLC

(57) ABSTRACT

Facile methods for high-yield furfural and HMF production from biomass sugars are described. The methods generally involve converting the biomass sugars in high yield to their ketose isomers, resulting in furan production under low temperature and pressure conditions with efficient recycling of the process streams.

28 Claims, 18 Drawing Sheets

| Process step | Cost components | Cost basis | US $ per 1000 kg xylose processed | | Comments |
|---|---|---|---|---|---|
| | MgOH₂ | $0.150 per kg | | ($1.60) | Used for pH adjustment from pH 2 to 8.5 prior to SIRE |
| SIRE - Step 1 | Organic phase composed of octanol, N2B and Aliquat® 336 | | | | |
| | Octanol | $1.20 per kg | | ($23.01) | Make-up volume of 23.3 l; density 0.824 g/l |
| | N2B | $10.00 per kg | | ($37.84) | Make-up mass of 3.8 kg based on a 3.3:1 molar ratio of N2B to xylose |
| | Aliquat | $1.00 per kg | | ($8.89) | Make-up volume of 10 l based on a 1:1 molar ratio of Aliquat:N2B |
| | Immobilized xylose isomerase (XI) enzyme pellets | $27.00 per kg pellets | | ($3.38) | Based on 4.5 g XI pellets/l aqueous xylose solution; 1000 kg xylose processed/day; 300 day useable lifetime of pellets prior to replacement |
| | Sugar recovery credit | $1,000 per 1000 kg | | $200.00 | Recycle of xylose (stream 11, 200kg) for SIRE processing |
| Two step back-extraction (BE) - Step 2 | HCl | $0.115 per kg 35 wt % soln | | ($70.38) | Based on addition of 510 l total of 35 wt% HCl to accomplish stage 1 and stage 2 stripping and to achieve a stage 2 final pH suitable for dehydration (pH 1) |
| | Sugar recovery credit | $1,000 per 1000 kg | | $80.00 | Recycle of xylose (stream 12, 80 kg) for SIRE processing |
| Dehydration - Step 3 | pH adjust (HCl) | $0.115 per kg 35 wt % soln | ($35.99) | | Based on addition of 280 liter 3 volume of 1.36x10⁴ liters, assuming solution density and enthalpy properties same as pure water |
| | Energy input to stream 3 for dehydration (30 to 170 °C) | $5.97 per GJ | ($102.28) | | Based on stream 3 volume of 1.36x10⁴ liters, assuming solution density and enthalpy properties same as pure water |
| | Energy input to stream 8 for dehydration (30 to 110 °C) | $5.97 per GJ | | | Based on stream 8 volume of 4.8x10³ liters, assuming solution density and enthalpy properties same as pure water |
| | Energy input to vaporize stream 9 (ΔH_vap = 2258.9 kJ/kg) | $5.97 per GJ | | ($7.22) | Case A based on 28,800 kg water; Case B based on 4,430 kg water |
| Furfural Recovery | Furfural sales | $2.00 per kg furfural | ($389.09) | ($58.25) | Based on mass of furfural (stream 10) |
| Net gain/loss for the process | | | $912.00 | $626.69 | Based on process flow diagram and mass/energy balance calculations of figure 6 |
| | | | ($15.32) | $695.14 | |

FIG. 12

METHODS FOR HIGH YIELD PRODUCTION OF FURANS FROM BIOMASS SUGARS AT MILD OPERATING CONDITIONS

RELATED APPLICATIONS

This application is a divisional application of U.S. Ser. No. 15/033,376 filed Apr. 29, 2016, now U.S. Pat. No. 9,828,615 issued Nov. 28, 2017, a national stage application filed under 35 USC § 371 of international application PCT/US2014/063661 filed Nov. 3, 2014, which claims priority to U.S. Provisional Application Ser. No. 61/898,889, filed under 35 U.S.C. § 111(b) on Nov. 1, 2013, the disclosure of which is incorporated herein by reference in its entirety.

STATEMENT REGARDING FEDERALLY SPONSORED RESEARCH

This invention was made with government support under Grant Number CBET-1236708 awarded by the National Science Foundation. The government has certain rights in the invention.

BACKGROUND OF THE INVENTION

Traditional approaches to producing furans from the C5 and C6 sugars of lignocellulosic biomass have several limitations which include high reaction temperatures and pressures, significant sugar loss to side-reactions, modest furan yields, and high purification costs. For instance, the production of furfural from concentrated xylulose (30 g/l) has not previously been achieved, likely due to the difficulty of producing relatively large quantities of high-purity xylulose in a cost-effective manner.

The two furans, hydroxymethyl furfural (HMF) and furfural, produced via the dehydration of the 6-carbon and 5-carbon sugars of lignocellulosic biomass, respectively, are projected to be in higher demand with their increasing use in petroleum refining, plastics, and the agrochemical and pharmaceutical industries. These furans are also versatile and platform chemicals for the synthesis of many useful products and fuels, including dimethyl/methylfurans, gasoline, and diesel components. However, both continuous and batch processes in commercial implementation are inefficient (less than 50% theoretical yield for furan) and are severely limited by side-reactions, in particular humin formation, that consume sugar as well as furans.

Thus, there is an unmet need for high-yielding methods of producing furans from biomass sugars.

SUMMARY OF THE INVENTION

Provided herein is a method of producing furaldehydes (furans) from aldose sugars. The method involves (a) contacting an aldose sugar-containing solution with a first catalyst to form an aqueous isomerization reaction mixture comprising a ketose; (b) substantially simultaneously with step (a), contacting the aqueous isomerization reaction mixture with a first immiscible phase, wherein the first immiscible phase comprises a complexing agent (CA) capable of selectively binding with the ketose, to form a ketose-CA conjugate in the first immiscible phase; (c) maintaining the contact from step (b) at a first temperature and for a first period of time sufficient to drive aldose-ketose isomerization towards the formation of more ketose; (d) contacting the first immiscible phase with a second immiscible phase capable of stripping the ketose from the ketose-CA conjugate and selectively dissolving the ketose while leaving behind the CA in the first immiscible phase; (e) maintaining the contact from step (d) at a second temperature and for a second period of time, with or without a second catalyst, sufficient to back-extract at least half of the ketose into the second immiscible phase; and (f) heating the second immiscible phase to a third temperature to dehydrate the ketose into a corresponding furaldehyde.

In certain embodiments, the aldose sugar comprises xylose, and the corresponding furaldehyde comprises furfural. In certain embodiments, the aldose sugar comprises glucose, and the corresponding furaldehyde comprises hydroxymethyl furfural (HMF). In certain embodiments, the aldose sugar is present in a lignocellulosic biomass hydrolysate. In certain embodiments, the aqueous isomerization reaction mixture has a pH between about 7.5 and about 9.0. In certain embodiments, the first temperature is between about 50° C. and about 60° C. In certain embodiments, the method is conducted without a second catalyst.

In certain embodiments, the first catalyst comprises glucose isomerase or xylose isomerase (GI/XI) enzyme. In certain embodiments, the GI/XI enzyme is in the form of immobilized enzyme pellets suspended in the aqueous isomerization reaction mixture. In certain embodiments, the GI/XI enzyme is in the form of a packed bed of particles through which the aldose sugar circulates.

In certain embodiments, the first immiscible phase is a solid support to which the CA is attached to form immobilized CA particles. In certain embodiments, the immobilized CA particles are suspended in the aqueous isomerization reaction mixture or packed in the form of a bed of particles through which the aqueous isomerization reaction mixture circulates.

In certain embodiments, the CA is an aryl boronic acid (ABA) selected from the group consisting of: aminophenylboronic acid, napthalene-2-boronic acid (N2B), 4-butoxy-3,5-dimethylphenyl boronic acid, 4-tert-butyl phenyl boronic acid, and 3,5-dimethyl phenylboronic acid. In certain embodiments, the ABA is modified with one or more functional groups. In certain embodiments, the one or more functional groups comprises $NH_2$ or $COOH$ incorporated into the aryl group such that the aryl boronic acids are capable of covalently bonding to a functionalized solid support. In certain embodiments, the functionalized solid support comprises one or more of an oxirane, an amine, an aldehyde, or a carboxyl group such that the support is capable of covalently bonding to the one or more functional groups.

In certain embodiments, the first immiscible phase comprises a liquid that is immiscible with the aqueous isomerization reaction mixture and is capable of dissolving the CA. In certain embodiments, the liquid is selected from the group consisting of octanol, decanol, dodecanol, dicholoromethane, ethyl acetate, o-nitrophenyl octyl ether (NPOE), and diethyl ether.

In certain embodiments, the first immiscible phase further comprises a lipophilic salt ($Q^+X^-$). In certain embodiments, more than half of the ABA and ABA-ketose conjugate complex to the lipophilic salt via ion-pair formation.

In certain embodiments, the method further comprises the step of adjusting the relative volume ratio of the aqueous isomerization reaction mixture and the first immiscible phase such that the concentration of ketose-CA conjugate is higher in the extraction phase than the initial concentration of aldose in the aqueous isomerization reaction mixture.

In certain embodiments, the method further comprises sequential contact of the aqueous isomerization mixture with multiple fresh volumes of the first immiscible phase to increase aldose-to-ketose conversion and overall ketose extraction.

In certain embodiments, the second immiscible phase comprises a hydrochloric acid solution. In certain embodiments, the pH of the hydrochloric acid solution is between about 1 and about 5. In certain embodiments, the pH is about 1. In certain embodiments, the hydrochloric acid solution comprises about 30 g/l back-extracted xylulose. In certain embodiments, when the pH of the hydrochloric acid solution is between about 4 and about 5, less tightly complexed ketose is selectively stripped out in a first stage back-extraction that leaves behind more tightly complexed ketose in the first immiscible phase. In certain embodiments, when the pH of the hydrochloric acid solution is between about 1 and about 2, more tightly complexed ketose is stripped out in high purity in a second-stage back-extraction.

In certain embodiments, furfural is produced at a yield of at least about 68% with a xylulose conversion of at least about 90%. In certain embodiments, at least a 78% furfural yield is obtained within about 10 minutes, with a xylulose conversion of above 90%. In certain embodiments, at least a 85% furfural yield is obtained within about 6 minutes, with a xylulose conversion above 90%.

In certain embodiments, the third temperature ranges from about 110° C. to about 130° C.

In certain embodiments, the method further comprises the step of adding an aprotic solvent to facilitate dehydration of xylulose to furfural. In certain embodiments, the aprotic solvent comprises dimethyl sulfoxide (DMSO). In certain embodiments wherein DMSO is used, furfural is produced at a yield of at least about 77% with a xylulose conversion of at least about 90%. In certain embodiments, the DMSO is added at about 33% by weight. In certain embodiments, the DMSO is added at about 66% by weight. In certain embodiments wherein DMSO is used, at least a 85% furfural yield is obtained within about 15 minutes, with a xylulose conversion above 90%.

In certain embodiments, the second immiscible phase comprises an ionic liquid having an acidic anion. In certain embodiments, the ionic liquid is selected from the group consisting of 1-ethyl-3-methylimidazolium hydrogen sulfate ([EMIM][HSO$_4$]), and 1-ethyl-3-methylimidazolium trifluoromethanesulfonate ([EMIM][TfO]). In certain embodiments, the ionic liquid is [EMIM][HSO$_4$], and the ketose is quantitatively stripped from the first immiscible phase while leaving behind substantially all of the CA in the first immiscible phase. In certain embodiments, the ionic liquid is [EMIM][TfO], and at least 50% of the ketose is stripped in a single-stage contact from the first immiscible phase while leaving behind substantially all of the CA in the first immiscible phase. In certain embodiments, the method comprises multiple stages of contacting the first immiscible phase with the ionic liquid. In certain embodiments, at least 50% of the ketose is stripped into the ionic liquid. In certain embodiments, ketose is back-extracted into the ionic liquid at progressively higher loadings of up to about 20 percent by weight. In certain embodiments, the ionic liquid is recycled and reused multiple times as the second immiscible phase after the furaldehyde is removed from the ionic liquid. In certain embodiments, conversion to the furaldehyde occurs in the ionic liquid.

In certain embodiments, the method further comprises contacting the second immiscible phase with a third immiscible phase selected from the group consisting of: tetrahydrofuran (THF), toluene, methyl isobutyl ketone (MIBK)+ 2-butanol, 7:3 [v/v], MIBK, and 2-sec-butylphenol in proportions of 1:1, 1:2, and 1:3. In certain embodiments comprising the third immiscible phase contacting step, a 84% furfural yield is obtained within about 90 minutes, with a xylulose conversion above 90%. In certain embodiments, the second immiscible phase is [EMIM][HSO$_4$] and the third immiscible phase is tetrahydrofuran. In certain embodiments, the second and third immiscible phases are contacted at a 1:4 volume ratio. In certain embodiments comprising the third immiscible phase contacting step, a furfural yield of at least about 68% is obtained with a xylulose conversion above 90%. In certain embodiments wherein the second immiscible phase comprises an ionic liquid, the third immiscible phase is kept in contact with the ionic liquid to achieve in-situ extraction of furaldehyde from the ionic liquid as it is formed. In certain embodiments, the third immiscible phase consists essentially of tetrahydrofuran.

In certain embodiments, the third immiscible phase isolates the furaldehyde from the reaction media as it forms. In particular embodiments, the method further comprises the step of separating the furaldehyde from the third immiscible phase. In particular embodiments, the method further comprises the step of heating the third immiscible phase to a fourth temperature to evaporate the third immiscible phase and leave the furaldehyde. In particular embodiments, the fourth temperature ranges from about 60° C. to about 300° C.

In certain embodiments, the second temperature is about 50° C. and the second period of time is about 4 hours. In certain embodiments, the first and second temperatures are about the same. In certain embodiments, the second temperature is between about 50° C. and about 60° C. In certain embodiments, the second period of time is between about 30 minutes and about 180 minutes.

In certain embodiments, the method further comprises the step of adjusting the volume ratio of the first and second immiscible phases such that ketose is recovered in the second immiscible phase at a higher concentration relative to its concentration in the first immiscible phase or the initial concentration of aldose sugar in the aqueous isomerization reaction mixture. In certain embodiments, the method further comprises the step of increasing the volume ratio of the first immiscible phase to the aqueous isomerization reaction mixture.

In certain embodiments, the method is conducted with a second catalyst, and the second catalyst comprises a catalytic amount of one or more of HCl or a solid-acid catalyst. In certain embodiments, the second catalyst is Amberlyst 15 or 12-TPA. In certain embodiments, the second catalyst comprises a catalytic amount of NaCl.

In certain embodiments, the method comprises multiple stages of back-extraction. In particular embodiments, each stage of back-extraction occurs sequentially into a single volume of ionic liquid.

BRIEF DESCRIPTION OF THE DRAWING

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

(FIG. 6A.) The aqueous phase initially contained 10 mM xylose. The organic phase used was pure 1-octanol with a fixed ratio of Aliquat® 336 to N2B of 2.5. Equal volumes of aqueous and organic phases were used. Xylulose extraction selectivity is defined as the percentage of xylulose in the total sugars (xylose+xylulose) extracted into the organic phase. Sugar extraction efficiency is defined as the percentage of sugar initially added to the aqueous phase that is extracted into the organic phase. (FIG. 6B.) N2B in the organic phase was 165 mM; glucose in the aqueous phase was 30 g/l (166.7 mM). The volumes of the two phases were adjusted to achieve different N2B to sugar mole ratios. The concentration of Aliquat® 336 in the organic phase was varied to test several different molar ratios to N2B (A:N2B) as shown in the legend; sugar extraction is shown with closed symbols and ketose selectivity is shown with open symbols.

(FIG. 7A.) Summary of results for a 30 g/l (~165 mM) aqueous glucose stream contacted with octanol containing 165 mM N2B and 412.5 mM Aliquat® 336. (FIG. 7B.) These data show results for multi-stage extraction of fructose during SIRE and the concentration of sugar during the BE step. The aqueous phase (1) was pre-isomerized to equilibrium (2) prior to four sequential stages of SIRE, each with 3 hr contact between the organic and aqueous phases. The molar ratio of N2B to sugar in each stage of SIRE was adjusted to achieve optimal sugar extraction and fructose selectivity by changing the organic phase volume. N2B-to-sugar molar ratios used were as follows: Stage I (streams 2 & 10)—1:1; Stage II (streams 3 & 11)—2:1; Stage III (streams 4 & 12)—3:1; and Stage IV (streams 5 & 13)—3.5:1.

FIG. 9A: Direct dehydration of xylose to furfural. $^a$Based on adiabatic flash with $\Delta H=0$. $^b$Theoretical yield is 064 g furfural per gram xylose; furfural yield is based on 40% of theoretical yield. $^c$Stream is at the reference temperature of 50° C. used for energy balance calculations.

FIG. 9B: Enzyme-catalyzed liquid phase SIRE-BE followed by dehydration of xylulose to furfural. $^a$Based on adiabatic flash with $\Delta H=0$. $^c$Stream is at the reference temperature of 50° C. used for energy balance calculations. $^d$Volume of acid solution for streams 2a and 2b are based on a phase volume ratio of 6.94 to concentrate sugars during BE. $^e$Based on a 1:1: aqueous-to-organic volume ratio for SIRE, make-up volume assuming 0.1% loss of extraction solvent in processing 1000 kg xylose. Organic phase make-up consists of 3.8 kg N2B dissolved in 23.3 l octanol and 10 l Aliquat®. $^f$Solid $Mg(OH)_2$. $^g$Solid N2B dissolved in organic phase. $^h$Based on 80% total sugar extraction and 90% selectivity for xylulose during SIRE with 100% sugar recovery in 2-stage back-extraction. $^i$Unextracted C5 sugar (xylose+xylulose); recycled for next SIRE. $^j$Theoretical yield is 0.64 furfural per gram xylose; furfural yield is based on 68% of theoretical yield. kStream 2b pH<1. $^l$Enthalpy relative to 50° C. (reference temperature) negligible.

FIG. 12: Table 7, a comparative technoeconomic evaluation of furfural production by direct xylose dehydration versus SIRE-BE-based xylulose dehydration. Numbers in parentheses represent expenses. $^a$Based on 1:1 aqueous-to-organic phase volume ratio. Cost values are based on 0.1% make-up volume per 1000 kg xylose per day processed. $^b$Quotes from http://www.alibaba.com, June 2013. $^c$Based on Genencor® quote for Gensweet® IGI-VHF. $^d$Based on average natural gas data, USEIA, OH, June 2012-March 2013. $^e$Based on average US market price, 2010. $^f$Net gain/loss for process FIG. 9B is $415.14 without sugar recovery credit.

FIG. 14A: Each of the solutions contained 9.6 g/l furfural. After 2 hours, 21% loss of furfural was seen for the water solvent while only a 3% loss was seen for the water-DMSO media. Inset photos show reaction mixture at 15 min (1 & 2) and 2 h (3 & 4). Punctate solids are visible on the vial wall in the water phase reaction mixture at 2 h (4).

FIG. 14B: Photos of reaction mixtures with equimolar furfural and xylulose after 15 min at 130° C. showing formation of insolubles in the water phase reaction.

DETAILED DESCRIPTION

Figure 1:
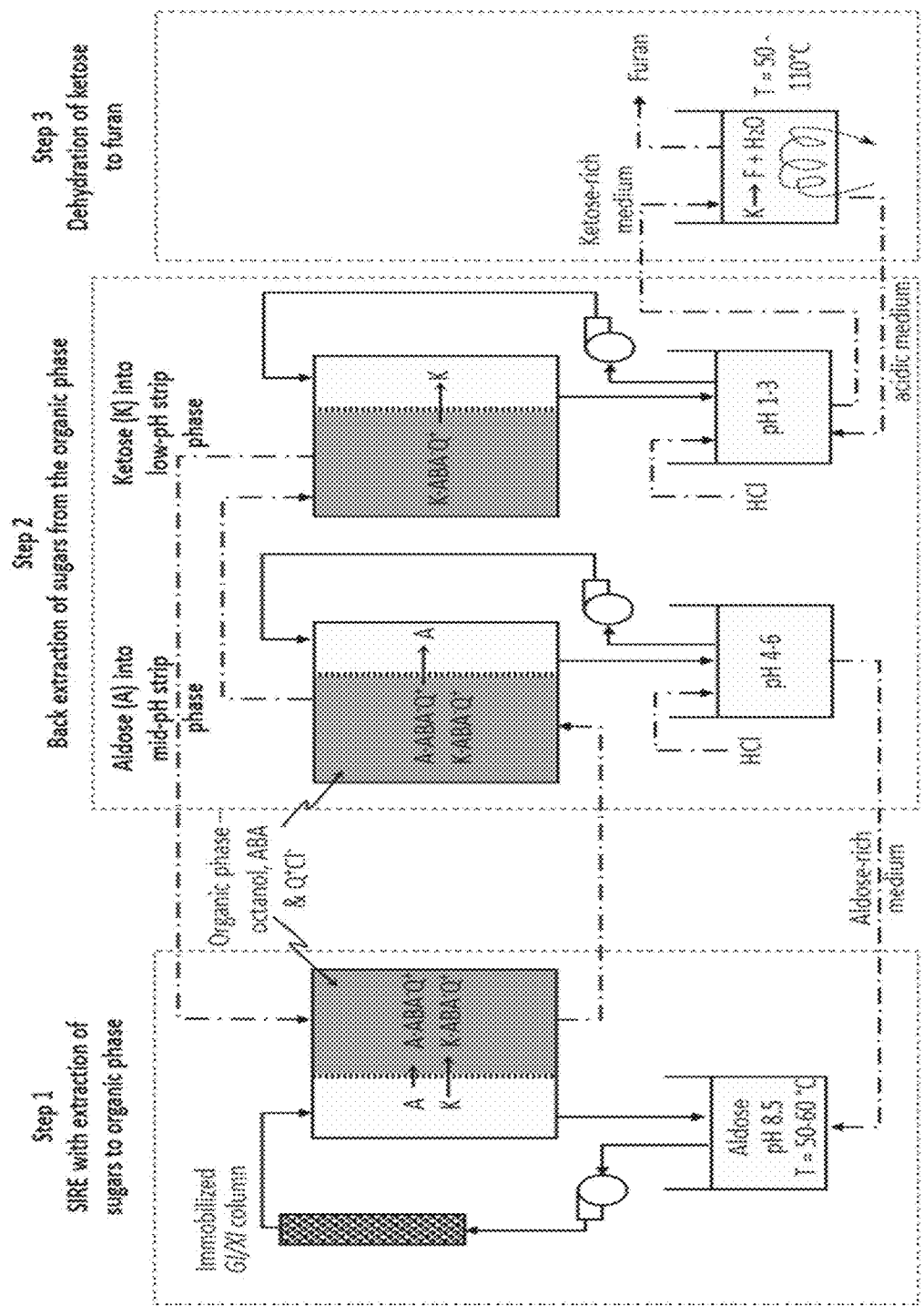
FIG. 1: Schematic representation of the three-step process for high-yield production of furan from biomass sugar. The process is shown starting with an aqueous aldose solution for simultaneous-isomerization-and-reactive-extraction (SIRE) in Step 1. The high affinity of ABA for ketose compared to aldose results in selective extraction of ketose into the organic phase in Step 1. The extracted sugar-ABA complex is stabilized in the organic phase via ion pairing with Aliquat® 336 ($Q^+Cl^-$). Following SIRE, two-stage back-extraction (BE) effectively separates ketose from aldose; ketose is recovered as a concentrated solution at low pH. The stripped aldose and the organic phase are recycled and reused. Ketose is converted to furan by heating in Step 3. Step 3 can be conducted in the furan-selective immiscible phase to selectively isolate furan and allow recycle of the reaction media. Solid arrows indicate fluid flow paths; dashed arrows represent addition/withdrawal of material at a specific time.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Current methods for producing furans (hydroxyl-methyl furfural (HMF) and furfural) from lignocellulosic biomass are limited in the efficiency of furan production due to incomplete conversion of the reactant sugars as well as undesired by-product and humin formation. Hydrogenation products of these furans, such as dimethylfuran and dimethyletetrahydrofuran, are useful as "drop-in" liquid transportation fuels. Conversion of biomass sugars with high yields to their ketose forms can immensely facilitate one-pot synthesis of furans from these sugars. Aldose-to-ketose isomerization, however, has a very unfavorable equilibrium, and high yield conversion to ketoses in a manner that allows for further conversion economically has yet to be realized in the art.

Without wishing to be bound by theory, Brønsted acid-catalyzed xylose/glucose dehydration to the corresponding furan is believed to occur through a direct cyclic mechanism via a furan aldehyde intermediate. Alternately, isomerization of xylose/glucose to xylulose/fructose (via an open chain mechanism) by Lewis acid catalysts and subsequent xylulose/fructose dehydration has also been used to produce furfural/HMF. Dehydration of ketose sugars to furans has a lower activation energy compared to aldoses and, in principle, can be carried out at higher sugar concentrations and at lower temperatures with reduced by-product/humin formation and higher yields of furans. A serious hurdle in the isomerization-dehydration route is the unfavorable equilibrium of the isomerization which favors the aldose sugar. To drive the isomerization reaction toward ketose, product removal strategies that combine isomerization and dehydration have been attempted. At moderately high temperatures (>140° C.) a combination of Lewis and Brønsted acid catalysts have been employed to increase furan yields. The mixed Lewis and Brønsted acid catalyst configuration for xylose-to-furfural conversion indicates that the Lewis acid sites promote not only isomerization but also formation of sugar and furan degradation products as well as non-useable isomers, while the Brønsted acid sites promote ketose-to-furan conversion. Since the Lewis acid sites promote competing reactions, the proportion of Lewis to Brønsted acid sites is important for maximizing furan yield through the ketose intermediate.

Described herein is a facile approach for high-yield furfural and HMF production via the ketose intermediates that is not hindered by the limitations predominant in the mixed-catalyst reaction systems. In this method, the isomerization is separated from the dehydration reaction, and each reaction is conducted under conditions and with catalysts that provide optimal yields. First, to ensure high yield of ketose sugar at facile conditions, enzyme-catalyzed isomerization of the aldose sugars is coupled with in situ reactive solid-phase or liquid-liquid extraction (simultaneous-isomerization-and-reactive-extraction, or SIRE) of ketose into a phase immiscible with the aqueous reaction medium. Second, quantitative back-extraction (BE) of ketose sugars is achieved into a desirable media capable of affecting high-yield dehydration under very mild operating conditions.

U.S. application Ser. No. 13/641,849, which is expressly incorporated herein in its entirety, describes methods for producing the C5 and C6 ketose sugars xylulose and fructose in purified, isolated, concentrated form from biomass hydrolysates. Described herein are methods for the subsequent furan production. Further provided herein are examples of how these sugars can be converted to furans in high yields through such processes that can be carried out at facile operating conditions, while also permitting recovery and reuse of the reaction and solvent media. Further provided is a comparative techno-economic analysis on the implementation of the method herein versus traditional xylose dehydration, with respect to furfural, showing significant economic advantages.

In particular, provided herein is a method for converting aldose sugars (such as the C5 and C6 biomass sugars xylose and glucose) to furaldehydes (such as furfural and HMF, respectively), at facile conditions in very high yield. The method involves a simultaneous isomerization and reactive-extraction (SIRE) followed by a back-extraction (BE), and produces high yield, high concentration ketose sugars in pure form from biomass hydrolysate without significant energy inputs. In this method, the aldose sugars are isomerized to their ketose isomers in high yield via a simultaneous-isomerization-and-reactive-extraction (SIRE) scheme, ketose is concentrated and purified by back-extraction (BE) into an acid or ionic-liquid medium, and then the ketose sugar is rapidly dehydrated to the corresponding furan at low temperatures (about 50-110° C.) with or without any additional catalyst. In certain embodiments, an aprotic solvent is added to the aqueous dehydration medium or in situ extraction of furan during the dehydration, giving furan yields of up to 90%. The mild process conditions associated with each of the steps in the process (SIRE, BE, and dehydration), along with the ability to concentrate the incoming sugar stream and recycle process streams and catalysts, results in minimal chemical and energy inputs and a significantly favorable impact on the overall process economics.

As shown in FIG. 1, the method provided herein generally entails the following steps: (1) simultaneous-isomerization-and-reactive-extraction (SIRE); (2) back-extraction (BE) of sugars; and (3) ketose dehydration. In certain embodiments, these steps can be broken down into the following steps: (a) contacting an aldose sugar-containing solution with a first catalyst to form an aqueous isomerization reaction mixture comprising a ketose; (b) substantially simultaneously with step (a), contacting the aqueous isomerization reaction mixture with a first immiscible phase, wherein the first immiscible phase comprises a complexing agent (CA) capable of selectively binding with the ketose, to form a ketose-CA conjugate in the first immiscible phase; (c) maintaining the contact from step (b) at a first temperature and for a first period of time sufficient to drive aldose-ketose isomerization towards the formation of more ketose; (d) contacting the first immiscible phase with a second immiscible phase capable of stripping the ketose from the ketose-CA conjugate and selectively dissolving the ketose while leaving behind the CA in the first immiscible phase; (e) maintaining the contact from step (d) at at second temperature and for a second period of time, with or without a second catalyst, sufficient to back-extract at least half of the ketose into the second immiscible phase; and (f) heating the second immiscible phase to a third temperature to dehydrate the ketose into a corresponding furaldehyde.

The term "aldose" refers to a monosaccharide that contains only one aldehyde. In particular embodiments, the aldose sugar comprises xylose, glucose, or a combination thereof. In particular embodiments, the aldose sugar is present in a lignocellulosic biomass hydrolysate. The ketose formed from isomerization depends on the identity of the aldose sugar used. In particular embodiments, the ketose formed in the isomerization reaction mixture is a hexose such as fructose or a pentose such as xylulose, but many other ketoses are possible.

Suitable first catalysts for the isomerization step include, but are not limited to, glucose isomerase (GI) enzyme, xylose isomerase (XI) enzyme, or combinations thereof. In certain embodiments, the first catalyst is in the form of immobilzed pellets confined to a packed bed. The identity of the first catalyst can generally be selected based upon the identity of the aldose sugar. In particular embodiments, the isomerization step occurs at a pH between about 7.5 and about 9.0. In particular embodiments, the isomerization step is conducted at a temperature between about 50° C. and about 60° C.

Suitable first immiscible phases include, but are not limited to, any liquid that is immiscible with the aqueous isomerization reaction mixture but dissolves the complexing agent. By way of a non-limiting example, the first immiscible phase can include one or more of octanol, decanol, dodecanol, dichloromethane, ethyl acetate, methyl iso-butyl ketone (MIBK), o-nitrophenyl octyl ether (NPOE), or diethyl ether. In certain embodiments, the first immiscible phase comprises a solid support to which the complexing agent is physically or chemically attached to form immobilized CA particles.

Figure 2:
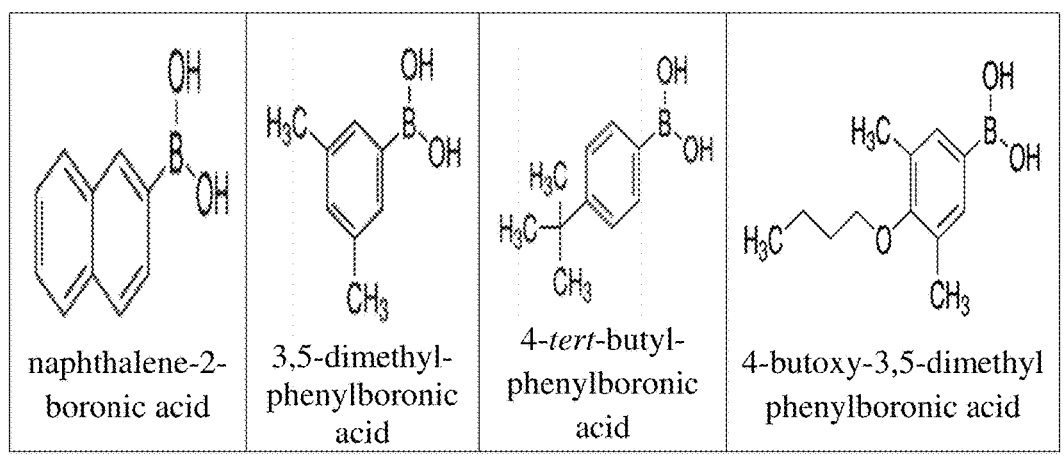
FIG. 2: Structures for the complexing agents used.

Suitable complexing agents include, but are not limited to, aryl boronic acids (ABAs) such as aminophenylboronic acid, napthalene-2-boronic acid (N2B), 4-butoxy-3,5-dimethylphenyl boronic acid, 4-tert-butyl phenyl boronic acid, and 3,5-dimethyl phenylboronic acid. The structures of these exemplary complexing agents are depicted in FIG. 2. In certain embodiments, one or more functional groups such as $NH_2$ or $COOH$ are incorporated into the aryl group of the ABA to enable covalent bonding of the aryl boronic acid to a functionalized solid support. In certain embodiments, the functionalization of the support is achieved with one or more of oxirane, amine, aldehyde, carboxyl, or similar complementary group that allows for the covalent attachment of the support to the functional group incorporated into the aryl boronic acid.

In addition to the ABA, the first immiscible phase can further include a lipophilic salt ($Q^+X^-$), which helps to confine the ABA and ABA-ketose complex to the first immiscible phase via ion-pair formation.

Suitable second immiscible phases include, but are not limited to, low pH hydrochloric acid (HCl) or hydrobromic acid (HBr) solutions in water or sulfolane, and ionic liquids having an acidic anion such as 1-ethyl-3-methylimidazolium hydrogen sulfate ([EMIM][$HSO_4$]), triisobutyl(methyl) phosphonium tosylate (CYPHOS 106), or 1-ethyl-3-methylimidazolium trifluoromethanesulfonate ([EMIM][TfO]), or combinations thereof. In particular embodiments, the pH of the hydrochloric acid solution ranges from about 1.0 to about 5.0. When the pH of the hydrochloric acid solution is maintained at moderately high values (4.0 to 5.0), the less tightly complexed aldose is selectively stripped out in a first-stage back-extraction, leaving behind the more tightly bound ketose in the first immiscible phase. When the pH of the hydrochloric acid solution is adjusted to lower values (1.0 to 2.0), the more tightly complexed ketose is stripped out in high purity in a second-stage back-extraction. When the second immiscible phase comprises an ionic liquid, the ionic liquid strips the ketose sugar quantitatively from the first immiscible phase while leaving behind the CA in the first immiscible phase. By way of a non-limiting example, [EMIM][TfO] can strip about 50% of the ketose sugar in a single-stage contact from the first immiscible phase, while leaving behind the CA in the first immiscible phase. Multi-stage contacting of the first immiscible phase with an ionic liquid such as [EMIM][TfO] can strip more than 50% of the ketose sugar into the ionic liquid. On the other hand, [EMIM][$HSO_4$] containing dissolved HCl can strip almost 100% of the fructose in a single-stage contact The method can further include the step of contacting the second immiscible phase with a third immiscible phase. Suitable third immiscible phases include, but are not limited to, toluene, a mixture of methyl isobutyl ketone (MIBK) and 2-butanol (such as in a 7:3 v/v ratio), MIBK, 2-sec-butylphenol, tetrahydrofuran (TFH), or a combination thereof. The use of a third immiscible phase improves the net yield of the furaldehyde. The use of a third immiscible phase also enables easy recovery of the second immiscible phase for reuse, thereby decreasing overall costs.

The second catalyst may or may not be present. When present, suitable second catalysts include, but are not limited to, a catalytic amount of HCl, HBr, HI, or $H_2SO_4$, a solid-acid catalyst such as Amberlyst 15 or 12-TPA, a catalytic amount of NaCl, NaBr, or NaI, a catalytic amount of the Lewis acids $AlCl_3$, $FeCl_3$, $CrCl_2$ or $CuCl_2$, or combinations thereof.

SIRE-BE

Figure 3A:
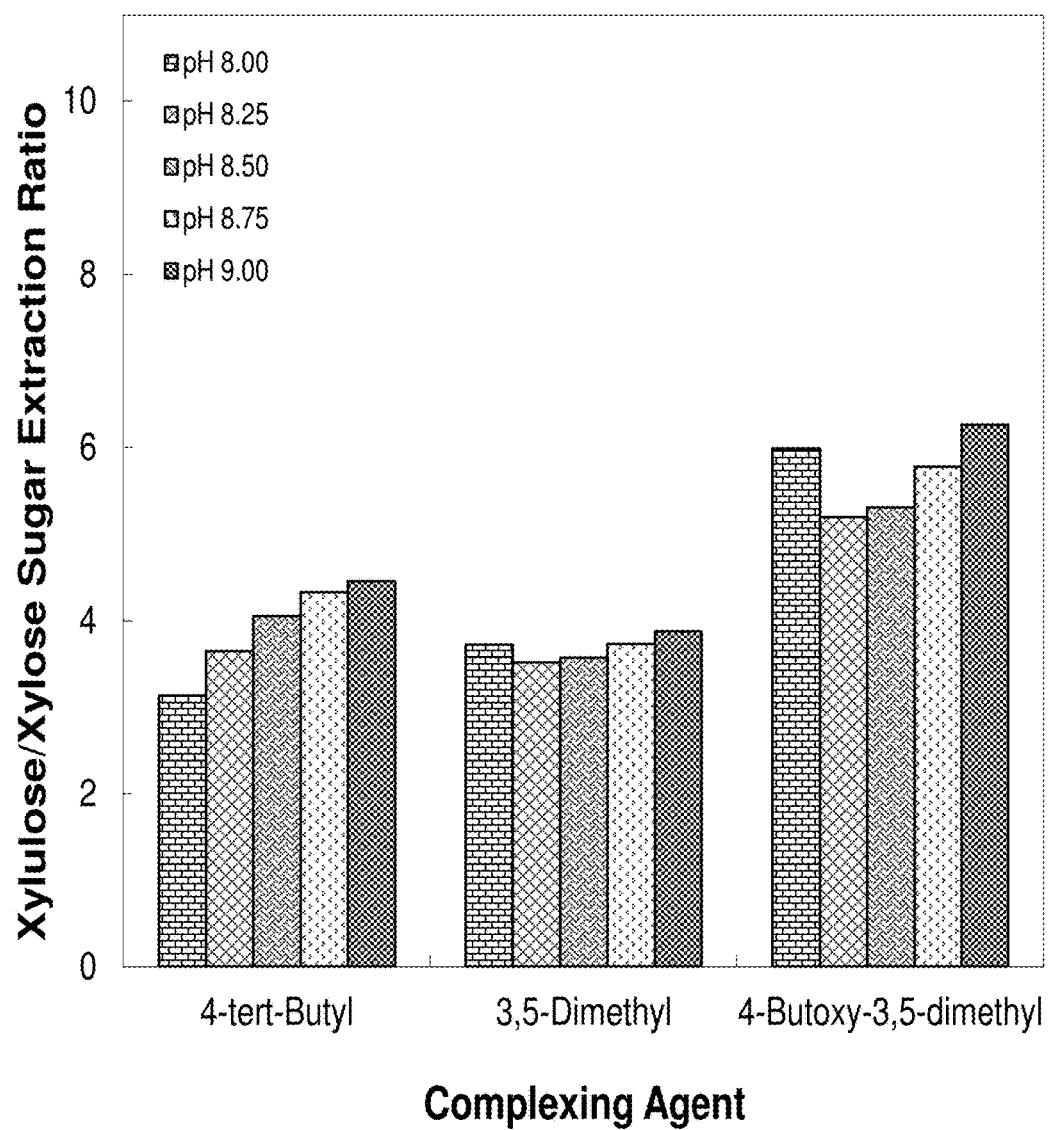
FIG. 3: Ketose to aldose single sugar extraction ratios for (A) C5 and (B) C6 sugars as a function of pH for three of the complexing agents. The individual 30 mM sugar solutions were made in either 50 mM sodium phosphate or sodium carbonate/bicarbonate buffer, depending on pH. The organic extraction phase consisted of 1-decanol containing the desired complexing agent and Aliquat 336®. The molar ratio of the sugar to complexing agent was 3:2; the molar ratio of Aliquat 336® to complexing agent was 2.5. Sugar was extracted using equal volumes of aqueous to organic phase until equilibrium was reached. Sugars were back-extracted from the organic phase using 100 mM HCl.
Figure 3B:
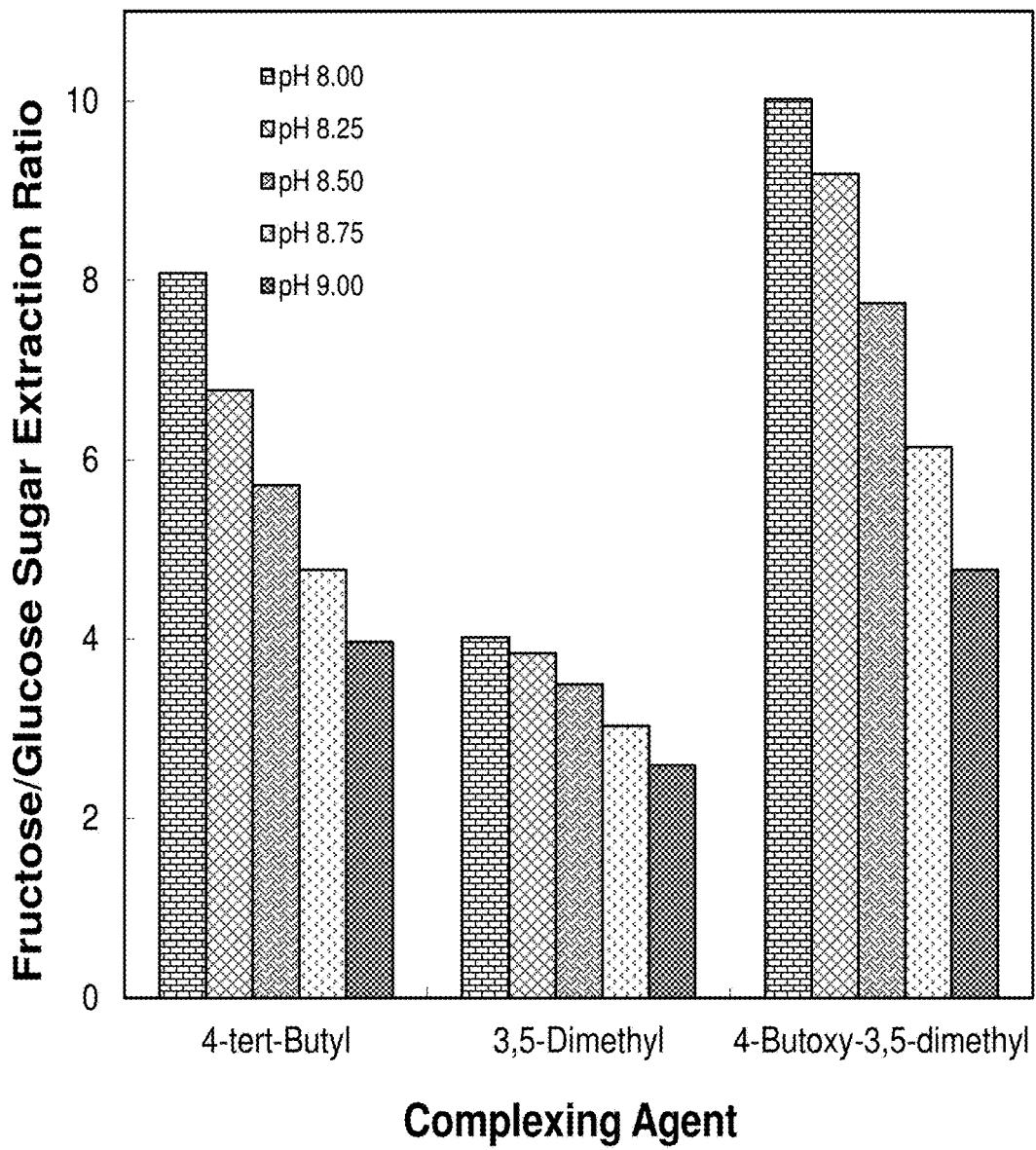
Figure 4:
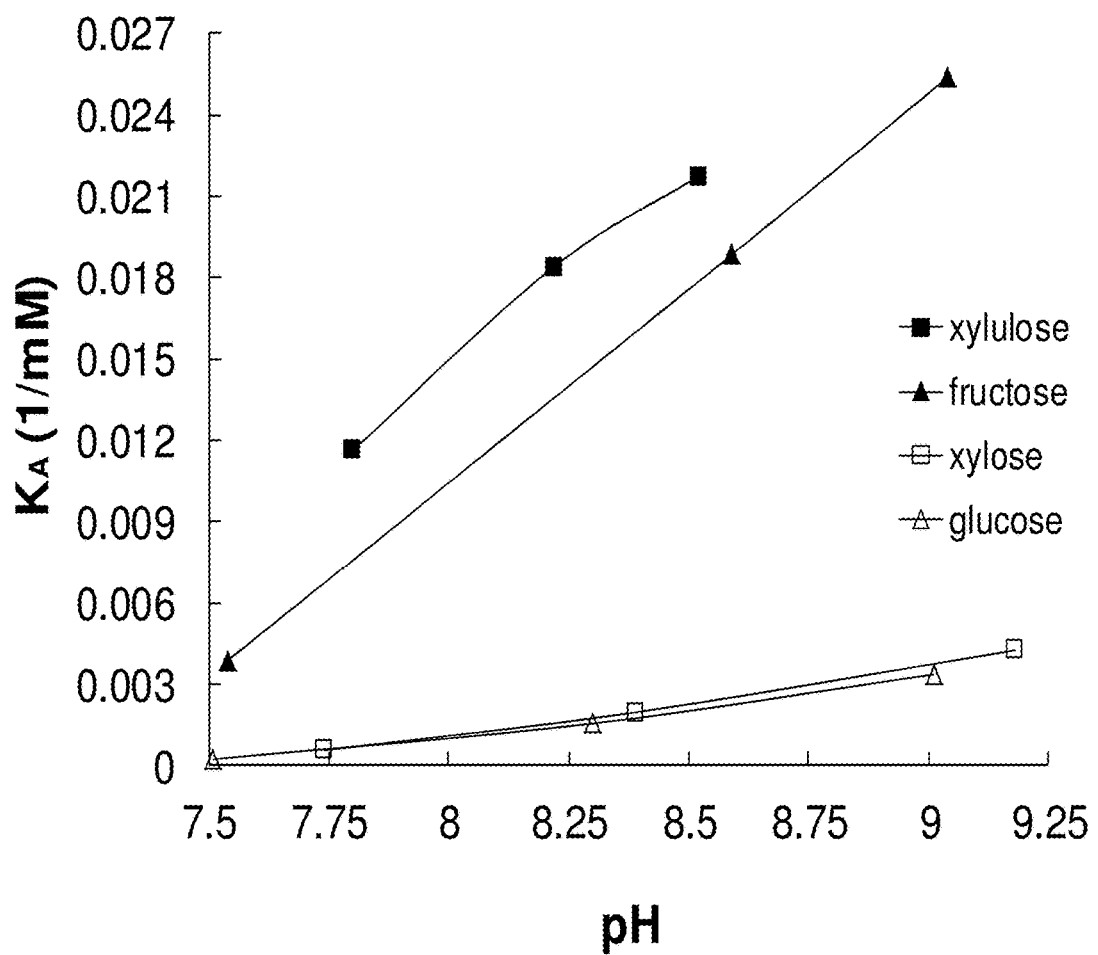
FIG. 4: Equilibrium association constants ($K_A$) for aldose and ketose sugars with N2B. Aqueous sugar solutions (30 mM) were mixed with an equal volume of octanol containing 20 mM N2B and 50 mM Aliquat® 336. Sugar remaining in the aqueous phase as well as sugar in the organic phase (determined after acid extraction) were measured to determine the equilibrium association constant between the sugar and the N2B.

For purposes of illustration, an example of the method will now be described. In Step 1, the aldose to ketose isomerization is effected very specifically (that is, with substantially no other isomers formed) with commercially-employed immobilized glucose/xylose isomerase (GI/XI) enzyme. The temperature at which the enzyme effectively catalyzes the isomerization (50-60° C.) not only eliminates loss of sugar to byproducts but also is compatible with saccharification, the last step for production of biomass hydrolysate. To overcome the unfavorable isomerization equilibrium, SIRE is employed to separate and concentrate ketose sugars as they are formed. The selective extraction of ketose sugar from the aqueous phase solution is facilitated by the addition of an aryl boronic acid (ABA) and Aliquat® 336 to the organic phase. ABA preferentially binds to ketose sugars, and ion-pair formation between Aliquat and the sugar-ABA complex confines the complex to the organic phase. The differential, pH-dependent affinity of the ABA for ketose and aldose (as seen in FIGS. 3-4) not only influences their selective extraction, but also increases the relative ease with which they can be dissociated from ABA and concentrated in aqueous and non-aqueous acid media through BE in Step 2.

When the ABA does not display high ketose-to-aldose selectivity, some aldose can also be extracted into the organic phase during SIRE. However, aldose has a relatively low affinity for the ABA and back-extracts under moderately-acidic conditions while the strongly-bound ketose requires more acidic conditions. By implementing a pH-staged BE process, ketose can be recovered as a nearly-pure, concentrated aqueous stream in stage 2. The concentrated stage 1 BE solution contains nearly all of the stripped aldose and is recycled back to the SIRE process.

Both the SIRE step and the BE step can be tailored to take place in single or multiple stages as needed for any given aldose/ketose transformation. Some specific examples of configurations for single and multi-stage implementation of each of the steps (SIRE and BE) are detailed in the examples below, but many other configurations are possible and these specified configurations are not meant to be in any way limiting.

Furan Production

High purity, concentrated xylulose/fructose is produced from xylose/glucose by SIRE-BE. The special media required for BE is capable of high-yield ketose extraction and subsequent ketose dehydration under facile conditions. Since HCl used for stage 2 ketose back-extraction also serves as the catalyst for dehydration (FIG. 1, Step 3), furan can be produced from the ketose-rich stream simply by heating it. In addition to acidified water, the ketose sugars can also be extracted into (1) mixtures of acidic aqueous and aprotic solvents (such as DMSO and sulfolane), and (2) several pure or acid-containing ionic-liquids (IL) that do not mix with the organic medium used during the SIRE step.

The methods described allow for the direct back-extraction of ketoses into acid-containing, benign reaction media, such as IL-media, which are especially suitable for high yield conversion of ketoses to furans under extremely mild conditions. Imidazolium-based ionic liquids stabilize furans in the reaction mixture and increase the reaction selectivity. Accordingly, several different imidazolium-based ionic liquids are suitable. In particular, certain imidazolium-based ILs with acidic anions are immiscible with the organic phase and are able to back-extract ketose sugars from the organic phase extremely well, even without any added acid. Thus, the ketose can be directly dehydrated to furan in the IL via mild heating (here the acidic anion catalyzes the dehydration reaction). Upon complete conversion of the ketose and removal of the furan from the IL, the IL can be recycled and reused to back-extract ketose from the organic phase repeatedly. Separation of the furan from the IL can be carried out relatively easily either by extracting the furan into an immiscible solvent as it forms, conducting entrainer-assisted vacuum reactive distillation, or through an evaporation process of the IL-furan mixture after completion of the reaction. Since ILs have negligible vapor pressure, an evaporative separation process provides pure furan. The methods further allow for highly selective conversion of back-extracted xylulose to furfural through homogeneous synthesis under relatively low temperature conditions with minimal side-product formation.

The examples below describe several experiments under extremely facile conditions where furans were produced from ketose sugars back-extracted into IL media. The examples further demonstrate the reusability of the IL media.

EXAMPLES

The following examples describe ketose/aldose selectivity of different ABAs confined to either a solid phase or liquid phase immiscible with aqueous isomerization media. These examples establish candidate ABAs suitable for different ketose production. For SIRE, the extraction of sugars depends on both the ABA and the organic solvent. The composition of the back-extraction media used in these examples was selected based on maximizing both ketose extraction and furan production. For furfural production from xylulose, a technoeconomic analysis is presented in one example, comparing the cost-effectiveness of this process to traditional xylose dehydration. Additional examples show the effect of fructose content on the production of HMF and the reusability of the IL reaction media for multiple rounds of HMF production.

Example 1

Evaluation of Several ABAs and Organic Solvents for Establishing a Viable Reactive Extraction Phase for Implementation of SIRE Several ABAs were evaluated for their characteristics with SIRE-BE and production of an extracted ketose solution suitable for dehydration to furan. Several suitable liquid-phase ABAs tested are shown in FIG. 2. These ABAs are all lipophilic and can be confined to the organic phase with the assistance of an ion pairing quaternary amine salt such as Aliquat® 336. To assess the suitability of these ABAs for use in SIRE, the first criterion assessed was the ability to preferentially bind ketose sugar over aldose sugar at a pH compatible with the sugar isomerization by the enzyme XI. As such, these complexing agents were evaluated for their ability to extract individual sugars from the aqueous to the organic phase over a range of pH values. Individual experiments conducted showed higher ketose extraction than aldose extraction; the ratios of these sugar extraction efficiencies are shown in FIG. 3 with the organic phase decanol. In panel A, relative extractions of xylulose to xylose are shown, with 4-butoxy-3,5-dimethylboronic acid (BDM-PBA) displaying the highest selectivity in xylulose binding. In panel B, these same ABAs were used for C6 sugar extraction. BDM-PBA shows remarkable selectivity in fructose extraction under these same conditions.

In certain embodiments, in addition to ketose selectivity, overall sugar binding capacity is also desirable to the efficient design of the SIRE-BE system for a particular ABA. By measuring the total sugar extraction as well as the sugar selectivity, equilibrium association constants ($K_A$) can be calculated for the ABAs. Calculations for the $K_A$ of N2B for each sugar is shown in FIG. 4. These data were collected using 1-octanol as the organic phase. As shown in this figure, N2B has higher relative ketose/aldose selectivity for C5 than C6 sugars. Unlike BDM-PBA, it also has high total sugar binding capacity.

Example 2

Figure 5:
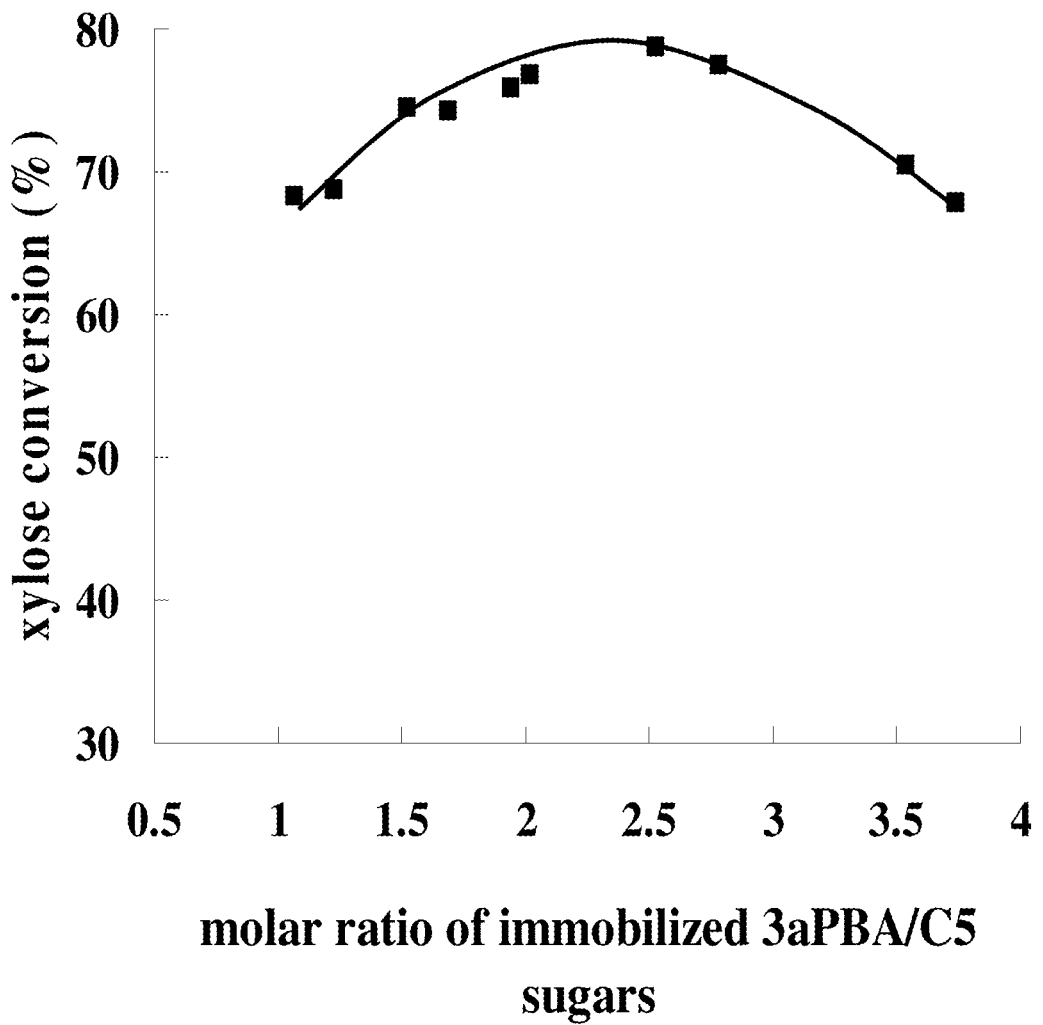
FIG. 5: Xylose conversion to xylulose using solid-phase SIRE. Xylulose conversion goes through a maximum which is dependent on the molar ratio of immobilized PBA and sugar.
Figure 6A:
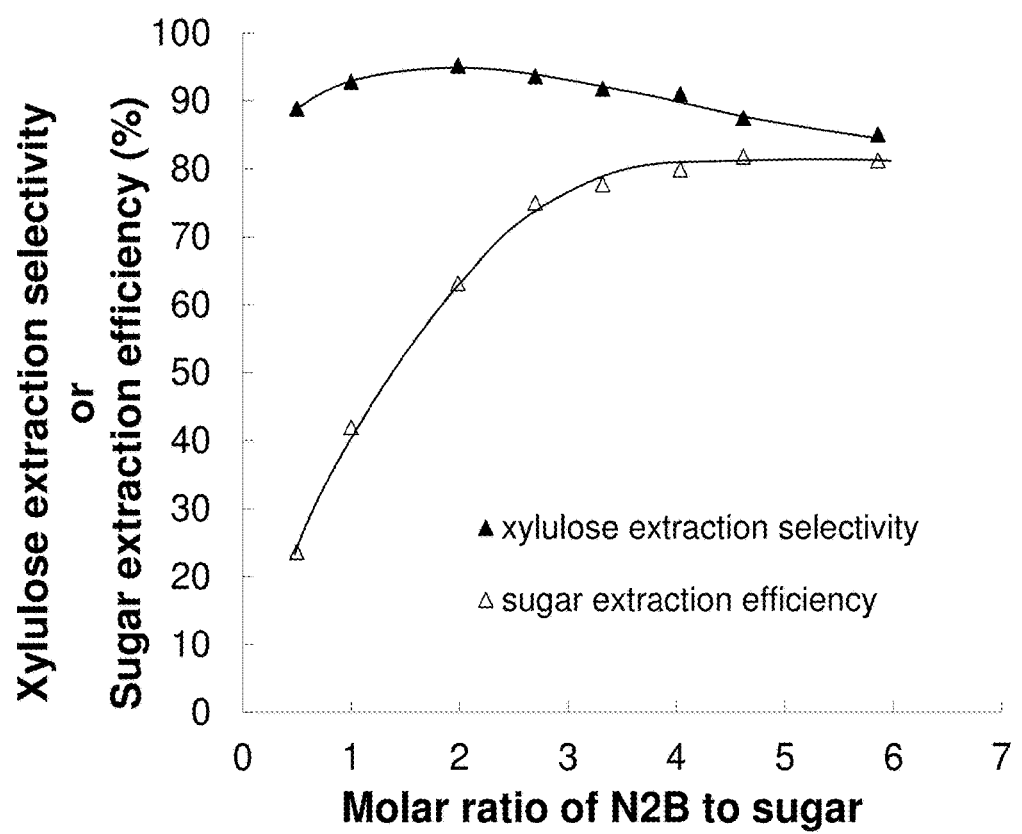
FIGS. 6A-6B: The effect of N2B-to-sugar molar ratio on liquid phase SIRE. Results shown are for equilibrium isomerization and extraction data in individual experiments.
Figure 6B:
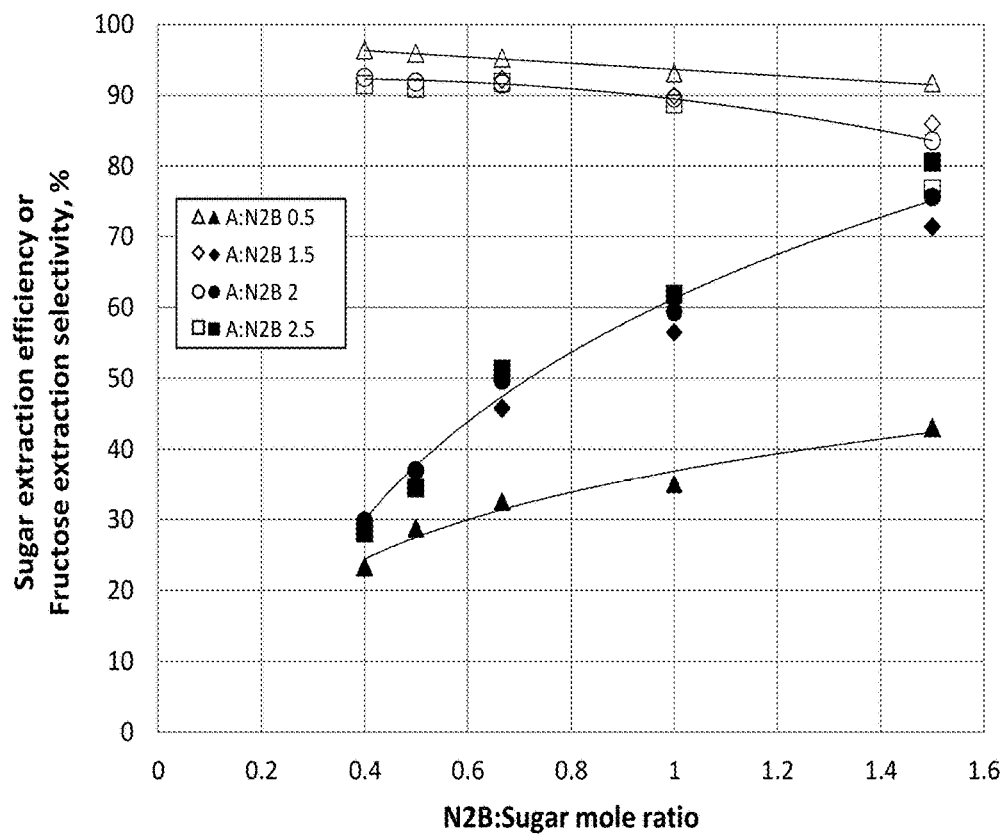

Optimum Sugar-to-ABA Ratio to Maximize Ketose Yield (PBA, N2B, FIGS. 5, 6A-6B)

3-amino phenyl boronic acid (3aPBA) was immobilized by covalently binding the amino group to an oxirane-functionalized solid support material to achieve solid-phase sugar complexing medium. A xylose sugar solution buffered to pH 8.5 was recirculated through two packed beds, one containing immobilized XI particles and one containing immobilized PBA particles, connected in series. Xylulose formed via XI-catalyzed isomerization binds preferentially to the immobilized PBA, thus driving the xylose to xylulose isomerization forward in the aqueous medium. Following SIRE, the xylulose bound to the immobilized PBA column was back-extracted by flushing the column with low pH medium. Through implementation of SIRE with various xylose-to-PBA ratios, an optimum ratio for xylulose production was established, as shown in FIG. 5.

To test the capacity for separation of aldose from ketose isomers, liquid-liquid SIRE was performed initially with pure xylose (10 mM, pH 8.5) (see FIG. 6A) or pure glucose (30 g/l, pH 8.5) (see FIG. 6B) using an organic phase diluent of 1-octanol. The ratio of N2B (in the organic phase) to sugar (initially added to the aqueous phase) was varied to determine its impact upon ketose selectivity and sugar extraction. As shown in FIG. 6A for a xylose/xylulose mixture, the total sugar extraction efficiency plateaued to ~80% for all N2B:sugar ratios great than 3.3, while the xylulose extraction hit a broad maximum near an N2B:sugar ratio of 2. Mixtures of glucose/fructose behave similarly (FIG. 6B), with ketose selectivity for fructose slightly lower than for xylulose under comparable conditions. Thus, the enhancement in isomerization achieved by confining the ketose sugar to a second phase depends on the ketose/aldose selectivity of the ABA as well as the molar ratio of ABA to sugar.

Example 3

Evaluation of IL Compatibility with the Extraction Phase (Miscibility) and Efficiency of Fructose Extraction In the prior examples, an HCl-acidified aqueous phase was used for the BE and dehydration medium. Since ionic liquids show considerable flexibility for green chemistry at low temperatures, several ILs were evaluated for their suitability as media to facilitate back-extraction and fructose dehydration. For these experiments, all sugars, solvents for SIRE and for in situ dehydration of fructose, furans, ABAs, Aliquat® 336, and ionic liquids were purchased from Sigma Aldrich Co (St. Louis, Mo., USA). HCl and the solid acid catalysts Wet Amberlyst 15 (Acros Organic Co.) and Amberlyst 70 (Dow Chemical Co.) were evaluated for their ability to improve the fructose extraction and to catalyze the dehydration. All other chemicals and solvents were purchased from Thermo Fisher Scientific Inc. (Pittsburgh, Pa., USA).

The first stage of the IL screening as a back-extraction and dehydration medium was for immiscibility with the organic phase containing the extracted fructose sugar. Octanol was used as the organic phase for screening ILs; more lipophilic solvents may result in different outcomes. Of the four ILs shown in Table 1, only [EMIM]HSO$_4$ and [EMIM]TFO were immiscible with octanol, making them candidates for the fructose extraction and subsequent dehydration. A fructose-loaded organic phase was generated by contacting 10 mM fructose in 50 mM sodium phosphate buffer (pH 8.5) sequentially with four volumes of organic phase containing 30 mM BDM-PBA and 65 mM Aliquat® 336 at 60° C. for 3 hrs. The aqueous phase pH was maintained at 8.5 by addition of 10 M NaOH as required. The organic and aqueous phases were separated by centrifugation at 5000 rpm. To back-extract the fructose from the organic phase, an equal volume of [EMIM]HSO$_4$ or [EMIM]TFO was contacted with the fructose-loaded organic phase. As shown in Table 1, below, [EMIM]TFO was only able to strip 50% of the fructose from the organic phase while [EMIM]HSO$_4$ completely extracted the fructose from the organic phase under the same conditions.

Table 1—IL screening for BE of fructose for dehydration. Fructose removal efficiency is the percentage of fructose present in the organic phase that is transferred to the ionic liquid.

| Ionic liquid | IL abbreviation | Miscible with Octanol? | Fructose removal efficiency (%) |
|---|---|---|---|
| 1-ethyl-3-methylimidazolium hydrogen sulfate | [EMIM]HSO$_4$ | No | 100 |
| 1-ethyl-3-methylimidazolium trifluoromethanesufonate | [EMIM]TFO | No | 50 |
| 1-ethyl-3-methylimidazolium chloride | [EMIM]Cl | Yes | N/A |
| 1-butyl-3-methylimidazolium methyl sulfate | [BMIM]CH$_3$SO$_4$ | Yes | N/A |

Example 4

High-yield Isomerization, Separation, and Concentration of Ketose from Aldose at Temperatures Compatible with Saccharification Tables 2 and 3 below summarize results for Steps 1 and 2 of FIG. 1 (SIRE-BE) starting from a very low concentration of aldose solution.

Example 4a

Xylose to Xylulose

The data shown in Table 2 are the results for the SIRE-BE process applied to xylose isomerization. High purity, concentrated xylulose was produced from xylose by simultaneous-isomerization-and-reactive-extraction (SIRE) followed by a two-stage back-extraction (BE) (see FIG. 1). SIRE was conducted using 1.56 g/l xylose in 50 mM sodium phosphate buffer at pH 8.5 and 50° C. with 4.5 g/l Gensweet® IGI (immobilized xylose isomerase). The aqueous sugar mixture was contacted with an equal volume of organic phase (octanol containing 34 mM N2B and 85 mM Aliquat® 336). The sugars extracted into the organic phase were back-extracted into HCl solution in two stages using a reduced stripping phase volume to concentrate the sugars. The net outcome of the process was the production of a 5-fold concentrated, >97% pure xylulose solution in HCl at pH 1. One significant advantage of this method over traditional dehydration of xylose is that un-isomerized xylose is not lost to side reactions but is recycled back into SIRE. As such, nearly quantitative conversion of xylose to xylulose is possible through judicious recycling of the aqueous streams leaving SIRE and the stage 1 BE.

Table 2—Summary of SIRE-BE results for a very low concentration xylose stream using N2B in octanol. The net result of this process is the production of 5-fold concentrated xylulose solution (5) in acid media, although the concentration factor was not optimized. Concentration of sugar can also be achieved during the SIRE step. All residual aqueous streams and the organic phase can be recycled to minimize water consumption and sugar loss. The aqueous sugar solution after SIRE (2) can be recycled to biomass pretreatment. The stage 1 back-extraction (4) has sugar preconcentrations on par with the initial sugar solution and can be combined with the next batch of biomass hydrolysate for SIRE. Since the organic phase is recycled for repeated extraction, residual sugar in the organic phase (6) remains within the system.

| Phase | Volume (ml) | Xylose (g/l) | Xylulose (g/l) | Xylose (mg) | Xylulose (mg) |
| --- | --- | --- | --- | --- | --- |
| 1. Initial sugar solution | 100 | 1.56 | 0 | 156 | 0 |
| 2. Aqueous after SIRE | 100 | 0.18 | 0.11 | 18 | 11 |
| 3. Organic before BE | 100 | | | 11.9* | 115.1* |
| 4. Stage 1 BE (aqueous) | 12.5 | 0.71 | 0.38 | 8.9 | 4.8 |
| 5. Stage 2 BE (aqueous) | 12.5 | 0.24 | 7.47 | 3 | 93.4 |
| 6. Organic after Stage 2 BE | 100 | | | | 16.9* |

*Calculated based on mass balance closure.

Example 4b

Glucose to Fructose

Figure 7A:
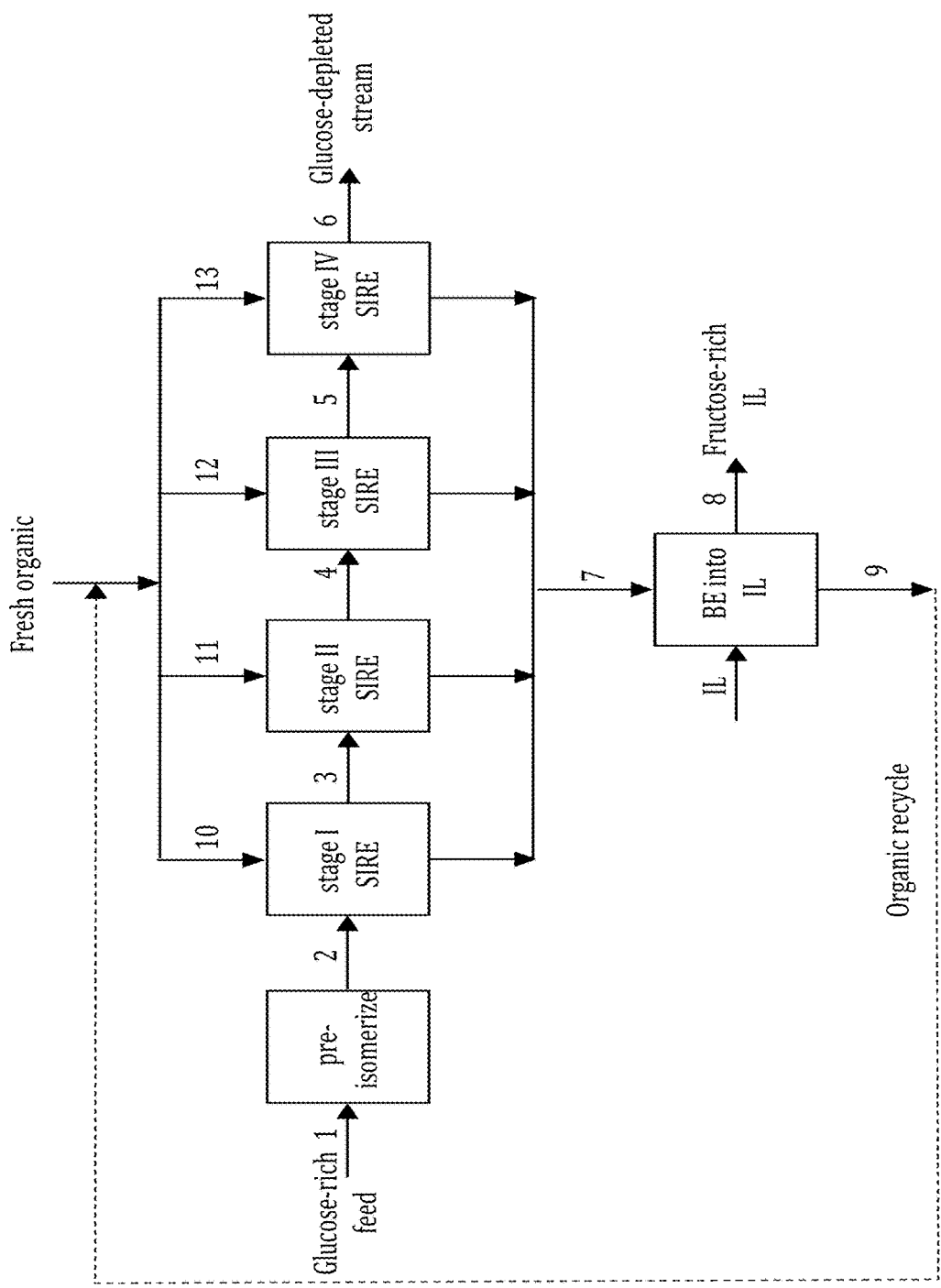
FIGS. 7A-B: Schematic representation of multi-stage cross-current SIRE process. Sugar back-extracted into IL is then dehydrated to furan.

The SIRE-BE method was also used to produce a high purity, concentrated stream of fructose from glucose at high yield. This process is illustrated in FIG. 7A and was implemented with for two different cases.

Case 1: To conduct SIRE, 10 mM glucose in 50 mM sodium phosphate buffer containing 4.5 g/l Gensweet® IGI (immobilized xylose isomerase) was pre-isomerized overnight to reach an equilibrium conversion of glucose to fructose. During the SIRE process the aqueous solution was maintained at pH 8.5 by addition of 10 M NaOH as required. The aqueous solution was contacted with an equal volume of organic phase (octanol) containing 30 mM BDM-PBA and 65 mM Aliquat® 336 at 60° C. for 3 hrs; this process was repeated sequentially four times with each step using a fresh organic phase to achieve a four-step cross current extraction. The organic and aqueous phases were separated at each step by centrifugation at 5000 rpm. After SIRE was complete, the four organic phases were combined for BE. The organic phase was contacted with a reduced volume of [EMIM]HSO$_4$ to concentrate the extracted fructose in the ionic liquid. The net results of this process are shown in Table 3. Isomerization without reactive extraction achieves a 46% fructose yield under these conditions. The SIRE-BE process yielded a fructose solution in the IL that was more than 96% fructose. In addition, relative to the starting glucose solution, more than 57% of the original sugar was recovered in a 2-fold concentrated form in the IL.

Figure 7B:
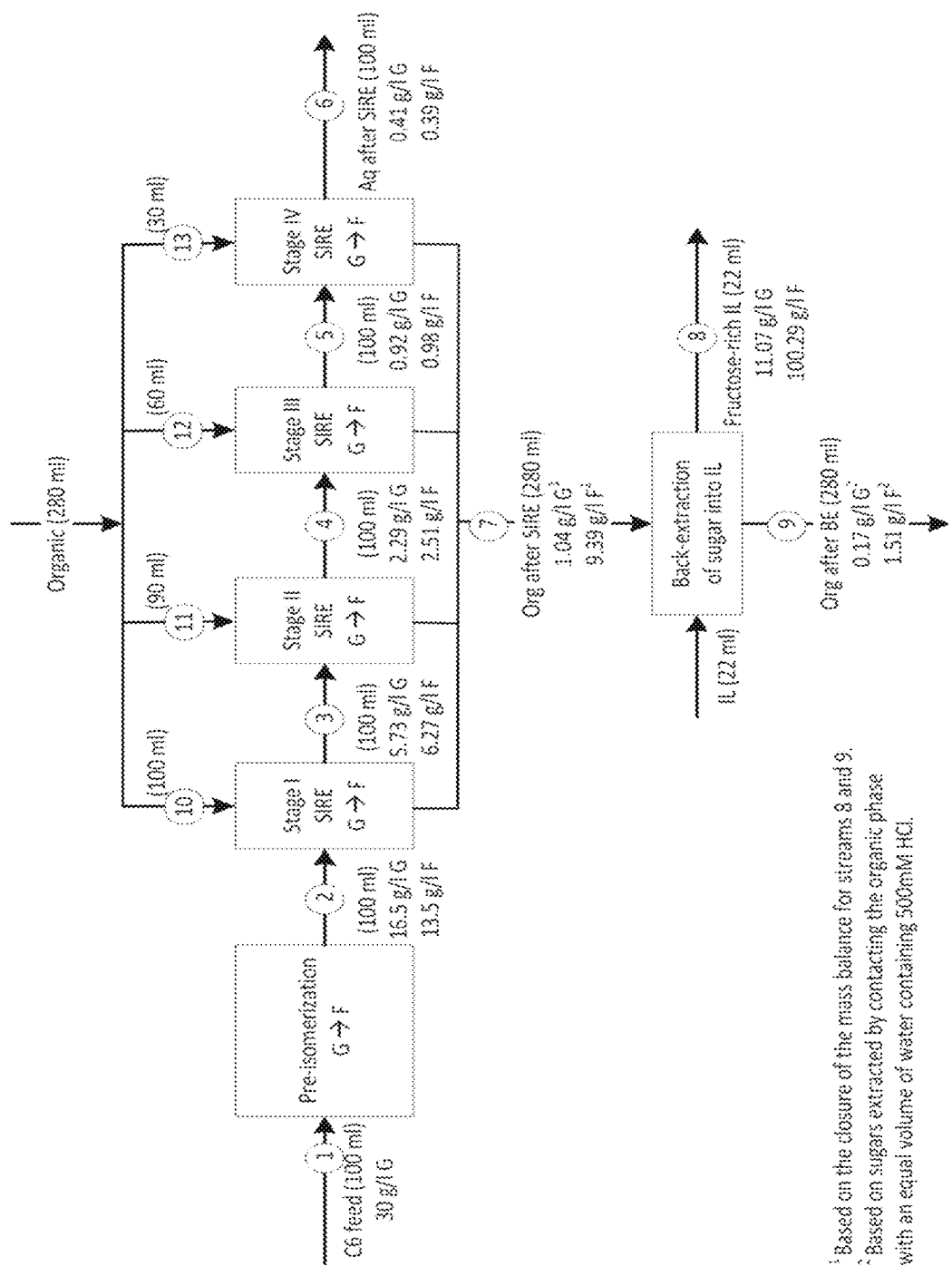

Case 2: The results of four sequential stages of SIRE with 30 g/l glucose in the aqueous phase and an organic phase of octanol containing 165 mM N2B and 412.5 mM Aliquat® 336N2B are shown in FIG. 7B. In each stage, a fresh volume of the organic phase was contacted with the aqueous sugar isomerization phase in a volume ratio that produced sugar extraction efficiency of 60% and fructose extraction selectivity of 90%. For glucose isomerization under these conditions without reactive extraction, fructose yield is around 45%. However, the 4-stage SIRE results in a shift in the overall isomerization of glucose to fructose from 45% to 88%. After 4 stages, 98% of the initial sugar is transferred to the organic phase; 88% of this sugar is fructose.

Table 3—Summary of SIRE-BE results for a very low concentration glucose stream using BDM-PBA in octanol. The net result of this process is the production of 2-fold concentrated fructose solution (4) in ionic liquid media ([EMIM]HSO$_4$), although the concentration factor was not optimized. These data show multi-stage extraction of fructose during SIRE and the concentration of sugar during the BE step. The aqueous phase was pre-isomerized to equilibrium (46% fructose) prior to contacting sequentially with 4 equal volumes of fresh organic phase. The composition of the combined organic phases (3) is shown prior to BE. The aqueous sugar solution after SIRE (2) can be recycled to biomass pretreatment. Since the organic phase is recycled for repeated extraction, residual sugar in the organic phase (4) remains within the system.

| Phase | Volume (ml) | Glucose (g/l) | Fructose (g/l) | Glucose (mg) | Fructose (mg) |
| --- | --- | --- | --- | --- | --- |
| 1. Initial sugar solution | 100 | 1.8 | 0 | 180 | 0 |
| 2. Aqueous after SIRE | 100 | 0.41 | 0.315 | 41 | 31.5 |
| 3. Organic before BE | 400 | 0.009 | 0.26 | 3.5* | 103.5* |
| 4. BE (IL) | 100 | 0.035 | ()1 | 3.5 | 100 |
| 5. Organic after BE | 400 | 0 | 0.009 | 0 | 3.5* |

*Calculated based on mass balance closure.

Example 5

Dehydration of Xylulose to Furfural in Aqueous Media at Low Temperatures

The dehydration experiments were carried out in well-mixed 10 ml thick-walled glass vials (Fisher Scientific). In a typical experiment, 1 ml of xylulose solution (at pH 1) was added to the reaction vial, and the vial was sealed. The vials were immersed in a pre-heated, constant temperature oil bath sitting on a stirring hotplate. For kinetic data, multiple vials were started simultaneously with each being removed after a different reaction time. Vials were quenched in an ice-water bath immediately upon removal from the heated oil bath.

Since HCl used for stage 2 xylulose back-extraction also serves as the catalyst for dehydration (FIG. 1, step 3), furfural can be produced from the xylulose-rich stream simply by heating. The direct conversion of high concentration, high purity xylulose solutions to furfural has not previously been attempted primarily due to the difficulty of producing high-purity xylulose in a cost-effective manner.

Figure 8:
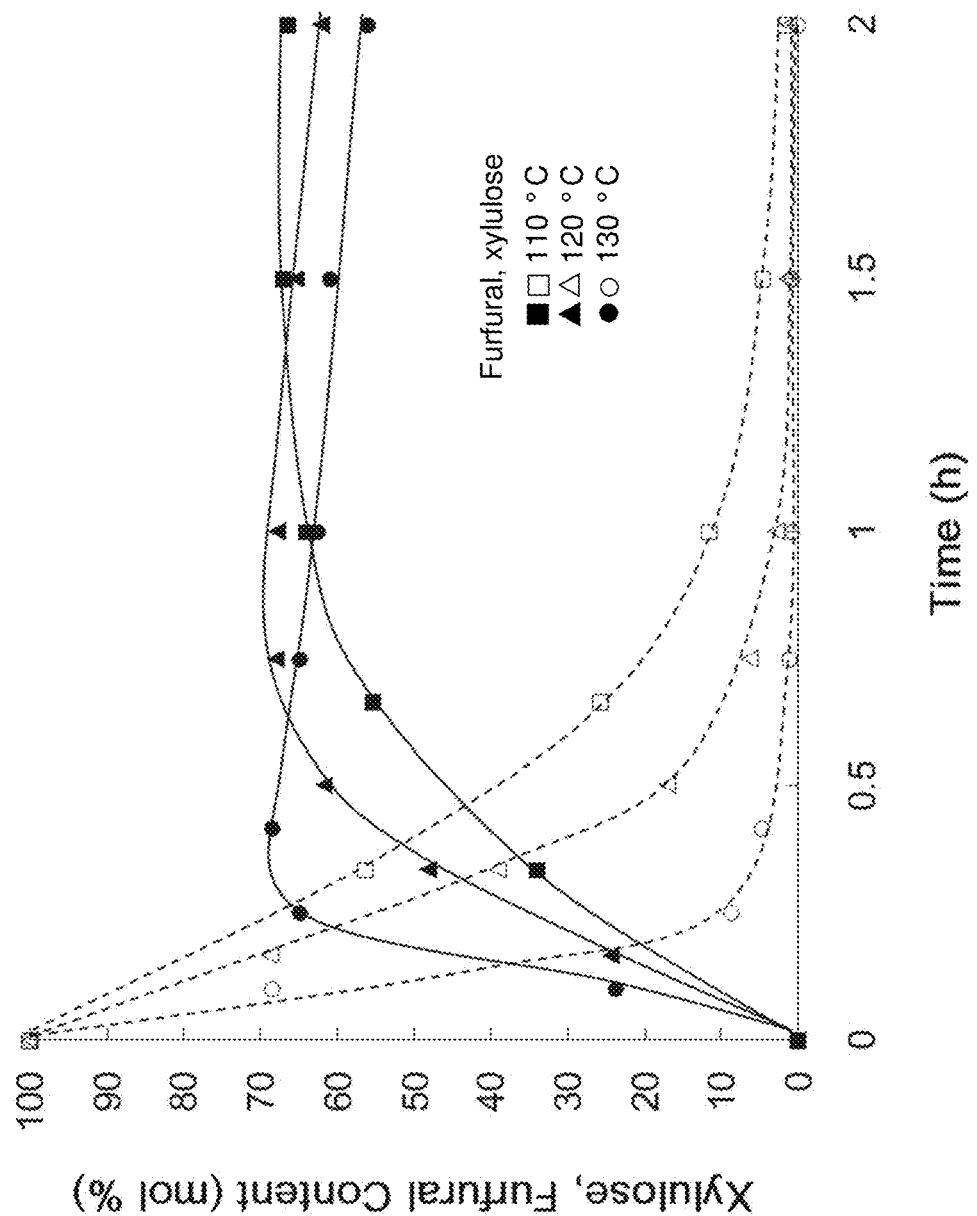
FIG. 8: Results for the catalytic dehydration of xylulose (dotted lines) to furfural (solid lines) with HCl at pH 1. Initial xylulose concentration in all experiments was 30 g/l. Each experiment was conducted in duplicate; standard deviation on individual values was less than 2%.

The results of the dehydration of SIRE-BE-produced xylulose to furfural for temperatures between 110-130° C. are shown in FIG. 8. Starting with 30 g/l xylulose at pH 1, >95% of the xylulose was consumed within 1.5 hr. The maximum measured furfural yield (mol furfural/initial mol xylulose) of 68% was temperature-independent. However, the time for maximum furfural yield decreased significantly with increased temperature, dropping from 90 min to 25 min. In contrast, prior attempts at xylose dehydration to furfural in aqueous reaction systems with temperatures up to 140° C. showed 3 hr xylose conversion ranging from 2% to 92% while the furfural yields achieved were only 0% to 37%. Considerably higher temperatures are important for further improving the furfural yield.

Example 6

Dehydration of Xylulose to Furfural in Mixed Reaction Media Containing Various Proportions of Aprotic Solvents and Water At elevated temperatures under acidic conditions, water molecules promote undesirable cross-polymerization reactions between the furan-product and the sugar-reactant in the reaction vessel. For this reason, aprotic solvents, such as dimethyl sulfoxide (DMSO), are useful to enhance product yield by lowering or eliminating the sugar- and/or furan-water interactions. Accordingly, xylulose dehydration at 110° C. and 130° C. was conducted with a modified aqueous phase consisting of either 1:2 or 2:1 volume ratios of water to DMSO. A summary of the experimental results is provided in Table 4, below. Surprisingly, the partial replacement of water with DMSO, even at a temperature as low as 110° C., led to a remarkable improvement in both furfural yield (from 68% to 85%) and reaction time (from 90 min to 15 min). Considering that the vapor pressure of the mixed DMSO/water solvent is considerably lower than atmospheric pressure, the dehydration is significantly simpler to implement than systems based on water only where higher temperatures and pressures are required.

Table 4—Summary of maximum measured furfural production and xylulose conversion from xylulose dehydration experiments. The maximum measured furfural yield may underestimate the true maximum yield due to the frequency of sample collection.

| $H_2O$:DMSO (v/v) | Temp (° C.) | Time (min) | Xylulose conversion (%) | Furfural yield (%) |
|---|---|---|---|---|
| 1:0 | 110 | 90 | 95 | 67 |
|  | 120 | 45 | 94 | 68 |
|  | 130 | 25 | 95 | 68 |
| 2:1 | 110 | 45 | 98 | 77 |
|  | 130 | 10 | 96 | 78 |
| 1:2 | 110 | 15 | 99 | 85 |
|  | 130 | 6 | 98 | 85 |

Example 7

Low Temperature Dehydration of Xylulose to Furfural with In Situ Furfural Extraction As an alternative to the addition of aprotic solvents, in-situ product removal from the aqueous reaction medium to an immiscible extraction solvent was also evaluated. Rapid removal of furfural from the aqueous reaction medium limits or eliminates potential side reactions that lead to reduction in furfural yield.

The dehydration experiments were carried out in well-mixed 10 ml thick-walled glass vials (Fisher Scientific). In a typical experiment, 1 ml of xylulose solution (at pH 1) and the appropriate volume of extraction solvent was added to the vial, and the vial was sealed. The vials were immersed in a pre-heated, constant temperature oil bath sitting on a stirring hotplate. For kinetic data, multiple vials were started simultaneously with each being removed after a different reaction time. Vials were quenched in an ice-water bath immediately upon removal from the heated oil bath.

Results from these experiments at 110° C. are summarized in Table 5 for four different solvents that display high partition coefficients for furfural. In situ extraction is also very effective (even at a 1:1 volume ratio) in improving furfural yields relative to a single-phase aqueous system (highest yield achieved was 90%). Favorable partitioning of furfural into the organic phase (100% for SBP) indicates easy isolation of furfural. Table 6 shows the results for a similar experiment using xylulose extracted into IL containing HCl as the catalyst. Note that although the overall conversion is not as high as in the aqueous phase dehydration reactions, the temperature used is considerable less, only 50° C. Thus, two-phase systems provide yield improvements similar to or better than DMSO, although the improvements in reaction time seen with the aprotic solvent were not possible with the bi-phasic system.

Table 5—Summary of maximum furfural yield with in situ furfural extraction by dehydration of 30 g/l xylulose in water at pH 1 and 110° C. The kinetics of furfural production are similar to those at the same temperature without in situ extraction. Total furfural yield is based on furfural in both the organic and aqueous phases.

|  |  | Reaction phase to organic phase volume ratio | | | | | |
|---|---|---|---|---|---|---|---|
| Reaction temperature |  | 1:1 | | 1:2 | | 1:3 | |
| 110° C. |  | Total yield (%) | Furfural in the organic phase (%) | Total Yield (%) | Furfural in the organic phase (%) | Total yield (%) | Furfural in the organic phase (%) |
| Extraction solvent | $T_{nbp}$, ° C. | | | | | | |
| Toluene | 111 | 74 | 80 | 78 | 88 | 79 | 91 |
| MIBK* + 2-Butanol (7:3 v/v) | 114 | 84 | 87 | 82 | 92 | 88 | 93 |

-continued

| Reaction temperature | Reaction phase to organic phase volume ratio | | | | | |
|---|---|---|---|---|---|---|
| 110° C. | 1:1 | | 1:2 | | 1:3 | |
| Extraction solvent | $T_{nbp}$, ° C. | Total yield (%) | Furfural in the organic phase (%) | Total Yield (%) | Furfural in the organic phase (%) | Total yield (%) | Furfural in the organic phase (%) |
| MIBK* | 117 | 84 | 88 | 86 | 94 | 90 | 94 |
| SBP* | 227 | 83 | 94 | 88 | 100 | 88 | 100 |

*MIBK—methyl isobutyl ketone; SBP—2-sec-butylphenol;

Table 6—Summary of maximum furfural yield with in-situ furfural extraction by dehydration of 30 g/l xylulose in IL with 3.9 mM HCl at 50° C. The yield shown occurs at less than 4 hrs. Total furfural yield is based on furfural in both the organic and aqueous phases.

| Reaction temperature 50° C. | | Reaction phase to organic phase volume ratio 1:4 | |
|---|---|---|---|
| Extraction solvent | $T_{nbp}$, ° C. | Total yield (%) | Furfural in the organic phase (%) |
| THF* | 66 | 65 | 92 |

*THF—tetrahydrofuran

Example 8

Techno-economic Comparison of Xylose Versus Xylulose Dehydration to Furfural

Material and energy balances were based on 1000 kg xylose/day resulting from dilute acid pretreated hemicellulose hydrolysate at pH 2 and 50° C. with xylose at 30 g/l. Necessary pH reductions for both xylose and xylulose dehydration were costed using a 35 wt % HCl solution (density of 1.2 kg/l).

Several simplifications were used in the technoeconomic analysis. Solid $Mg(OH)_2$ was chosen for initial pH adjustment from 2 to 8.5 for SIRE as $Mg^{2+}$ ions are activators for the XI enzyme (per manufacturer data sheet). XI cost was based on a 300 day process lifetime for the catalyst (per manufacturer data sheet). Since the organic phase used in SIRE-BE is recycled, cost calculations were based on 0.1% make-up volume per metric ton xylose processed. Unextracted and stage 1 back-extracted sugars were recycled in the SIRE process and cost-credit was taken for their recycle in the technoeconomic analysis.

All energy changes were computed using a reference temperature of 50° C. The aqueous sugar and furfural-containing streams were considered dilute and attributed physical properties of pure water, including a density of 1 kg/l; specific enthalpies of these streams were taken from steam tables. Energy calculations associated with furfural recovery following dehydration assumed an adiabatic flash of the reaction mixture followed by evaporation of water in the liquid stream resulting from the flash. Furfural was assumed to remain in the liquid streams. Mass to volume conversion for the pure furfural streams was based on furfural density of 1.16 kg/l.

The conventional method of producing furfural is a modified "Quaker Oats" process that is based on one-pot hydrolysis and dehydration of hemicellulose. Accordingly, feedstocks suited for this approach are biomass kinds that contain a very high percent of hemicellulose (such as oat hulls or peanut shells). Alternately, fractionation of the more traditional lignocellulosic feed-stocks such as corn stover, switch grass, or poplar via dilute-acid pretreatment can provide a separate process stream rich in the hemicellulose-derived sugars.

Since the present methods of SIRE-BE-based xylulose dehydration address process improvements relative to direct dehydration of xylose, a techno-economic comparison of the operating costs associated with these two approaches is presented below.

Figure 9A:
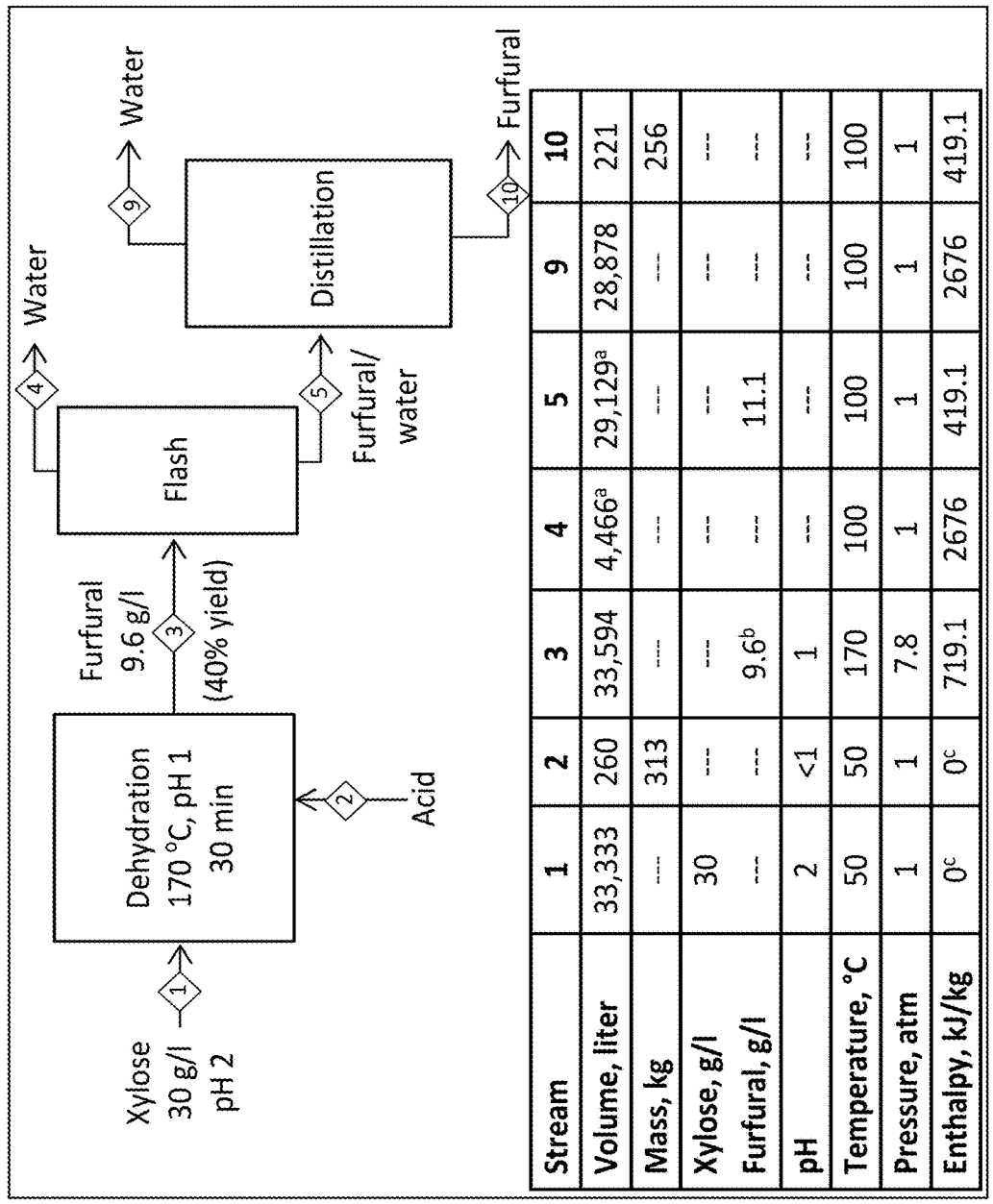
FIGS. 9A-9B: Process flow diagrams including stream characterization tables for the techno-economic calculations. The assumptions and data used in the mass and energy balance calculations are described in Example 8.

The analysis was based on 1000 kg (1 metric ton) per day xylose entering at 30 g/l and pH 2 as would be appropriate following dilute acid pretreatment of a typical lignocellulosic biomass. The xylose dehydration conditions and data of Weingarten et al, *Kinetics of furfural production by dehydration of xylose in a biphasic reactor with microwave heating*, Green Chemistry, 2010. 12(8): p. 1423-1429, in acidic aqueous media were used to compute the economics of the direct dehydration approach (FIG. 9A). Table 5 as well as Weingarten et al. also present data on sugar dehydration with in situ furfural extraction. In this example, the techno-economic comparison is restricted to monophasic systems.

Figure 9B:
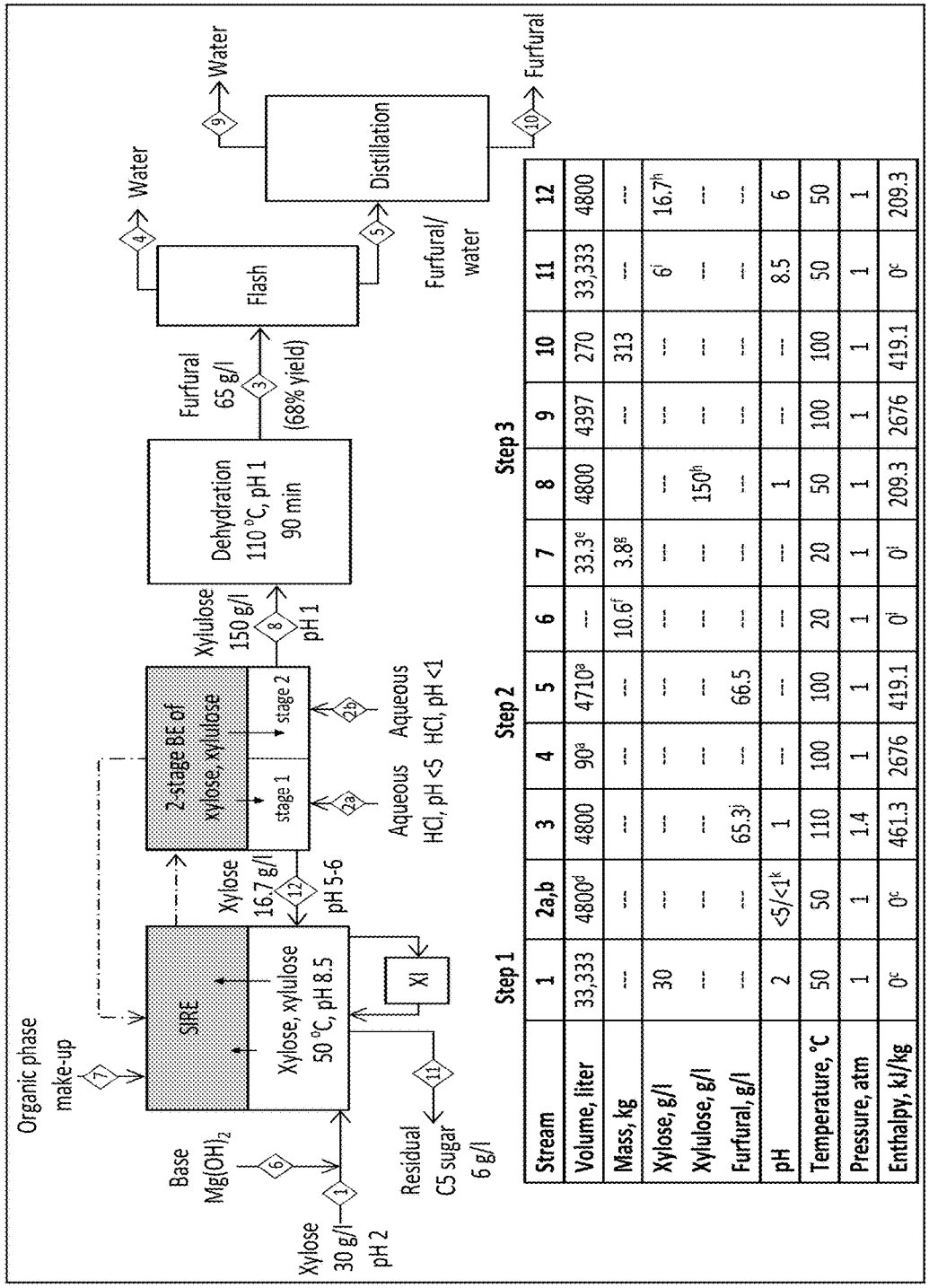

The basic process flow diagrams for the two approaches are shown in FIG. 9 along with the stream characterization tables. Details on assumptions used are provided in the FIG. 9 table footnotes. For the direct xylose dehydration base case (FIG. 9A), dehydration was conducted at 170° C. at pH 1 with a 40% theoretical yield of furfural. For the SIRE-BE-based process (FIG. 9B), the pH of the incoming xylose stream was adjusted from 2 to 8.5 through addition of solid magnesium hydroxide. Following isomerization and extraction, sugar recovery calculations were based on two-stage stripping (see FIGS. 1, 9B). The concentrated, nearly pure xylulose stream was then heated to 110° C. for dehydration with a 68% furfural yield (see Table 4). Energy costs associated with raising the reaction mixtures to the appropriate dehydration conditions were included in the analysis. For both processes, the reaction mixture was flashed to 1 atm to vaporize water. Additional energy costs were based on the evaporation of the remaining water in the liquid from the flash tank to recover pure furfural.

Table 4 provides a summary of the costs associated with each of the major unit operations of the processes shown in FIGS. 9A-B. As seen in Table 7, the major costs associated with direct dehydration of xylose stem from energy required for heating the reaction mixture to the dehydration temperature and for furfural recovery. In contrast, for the xylulose dehydration, the corresponding energy costs are significantly lower due to the following reasons: (1) significant concentration of sugars occurs during the back-extraction, reducing dehydration reaction volume by a factor of 7; (2) xylulose dehydration occurs at 110° C. as opposed to 170° C. for xylose; and (3) the higher furfural concentration in the product mixture reduces the amount of water removal needed to recover pure furfural. Based on the comparison of the operating expenses shown in FIG. 12, Table 7, a SIRE-BE-based process provides a significant cost advantage compared to direct dehydration of xylose, in spite of the additional unit operations involved.

Example 9

Efficiency of Fructose Dehydration to HMF in IL Reaction Media with In Situ HMF Extraction Acid and solid-acid catalysts were assessed for their ability to improve fructose dehydration to HMF in IL media. In addition, two organic solvents were employed to determine if in situ HMF extraction to an immiscible phase has the ability to improve HMF yields. To analyze HMF in the IL phase, high performance liquid chromatography (HPLC) was used. The samples were analyzed on an Agilent 1100 HPLC with an Aminex HPX-87H ion exclusion column (300 mm×7.8 mm) using a refractive index detector (RID). During the HPLC analysis, 5 mM $H_2SO_4$ at a flow rate of 0.55 ml/min was used for a mobile phase with the column temperature set to 65° C.

In experiments with in situ HMF extraction, the concentration of HMF was also analyzed in the organic phase. The HMF concentration in tetrahydrofuran (THF) was measured with an Agilent 1100 HPLC using an Agilent Zorbax SB-C18 reverse-phase column and a column temperature of 35° C.; a 2:8 (v/v) methanol:water solution at pH=2 at a flow rate of 0.7 ml/min was used to generate the hydrophobicity gradient. HMF was analyzed in MIBK by gas chromatography (GC) on a Shimadzu 2010 chromatograph with an RTX®-Biodiesel column (15 m×0.32 mm I.D.). The oven temperature was programmed from 60° C. to 300° C. at 25° C./min. Helium was used as the carrier gas at a flow rate of 1.0 ml/min. The injector was used in split mode; the injector temperature was set at 250° C. and the detector temperature was 300° C.

These experiments were divided into four cases, the results of which are summarized in Table 8, below. Each of these cases is discussed in more detail below.

Case A: In these experiments, 1000 mg [EMIM]$HSO_4$ and 100 mg fructose were heated to 50° C. for 180 min (A1), with an outcome of a 25% HMF yield. Addition of the catalyst 0.42 mM HCl (A2) or 0.42 mM HCl plus 0.7 M NaCl (A3) resulted in dramatic increases in HMF yield, 64% for A 2 and 74% for A3.

Table 8—Summary of the HMF yields achieved in IL media containing different catalysts/additives and reaction conditions. Fructose was extracted into the reaction media following SIRE-BE. Note that Cases B, C, and D include in situ extraction of HMF to an organic solvent during the dehydration.

| Case | Catalyst | Reaction conditions | In situ extraction solvent | HMF yield |
|---|---|---|---|---|
| A1 | — | 50° C., 180 min | — | 25 |
| A2 | 0.42 mM HCl | 50° C., 180 min | — | 64 |
| A3 | 0.42 mM HCl; 0.7M NaCl | 50° C., 180 min | — | 74 |
| B1 | — | 50° C., 180 min | THF | 30 |
| B2 | 0.42 mM HCl | 50° C., 180 min | THF | 68 |
| B3 | 0.42 mM HCl; 0.7M NaCl | 50° C., 180 min | THF | 79.5 |
| C1 | 12-TPA (50 mg) | 50° C., 180 min | THF | 31 |
| C2 | Amberlyst 15 (50 mg) | 50° C., 180 min | THF | 41 |
| C3 | Amberlyst 15 (50 mg) | 50° C., 360 min | THF | 46.5 |
| C4 | Amberlyst 15 (100 mg) | 50° C., 180 min | THF | 46 |
| D1 | 12-TPA (50 mg) | 100° C., 75 min | MIBK | 60 |
| D2 | Amberlyst 15 (50 mg) | 100° C., 75 min | MIBK | 72 |
| D3 | Amberlyst 70 (50 mg) | 100° C., 75 min | MIBK | 65 |
| D4 | 0.42 mM HCl | 100° C., 30 min | MIBK | 78 |

Case B: To evaluate the benefit of in situ HMF extraction under the conditions of Case A, experiments were repeated under the same conditions but with the addition of 12 ml of tetrahydrofuran (THF). In situ extraction of HMF into THF resulted in only a 3-5% increase in the overall HMF yield for the same conditions of Case A. THF was selected as the extraction solvent for these experiments because of its very low normal boiling point of 66° C. Although THF did not confer significant benefit in improving HMF yield, it did enable easy recovery of HMF by low energy-input evaporation of the THF following the dehydration reaction. HMF extraction into THF significantly simplifies reuse and recovery of the IL and THF, and recovery of HMF.

Case C: Experiments on fructose dehydration with in situ extraction of HMF were also conducted with solid acid catalysts to see if they were as effective as HCl in catalyzing the dehydration reaction at low temperature. Two catalysts, 12-TPA (C1) and Amberlyst 15 (C2-C3) were evaluated by adding 50 mg of solid acid catalyst to the reaction media. The catalyst 12-TPA offered negligible improvement in HMF yield over the IL alone (see B1 and C1). However, compared to only IL (B1), Amberlyst 15 increased the yield by 11%. By doubling the reaction time (360 min, C3) or doubling the catalyst loading (100 mg, C4), an additional 5% increase in HMF yield was obtained.

Case D: The dehydration of fruction to HMF was conducted at an elevated temperature of 100° C. Since the normal boiling point of THF is only 66° C., a different organic solvent, methyl isobutyl ketone (MIBK, normal boiling point of 117° C.) was used. Due to the increase in kinetics of the dehydration reaction at elevated temperature, the dehydration reaction was conducted for a shorter period of time in these experiments. Compared to the results in Case C with the solid acid catalysts 12-TPA and Amberlyst (see C1 and C2), fructose dehydration with in situ extraction into MIBK at 100° C. resulted in a 30% increase in HMF yield (see D1 and D2). A third solid-acid catalyst, Amberlyst 70 (see D3), gave an intermediate HMF yield (60% 12-TPA, 65% Amberlyst 70, and 72% Amberlyst 15). The best yield under these reaction conditions was seen with HCl (D4) with an even shorter reaction time (30 min).

Example 10

Figure 10:
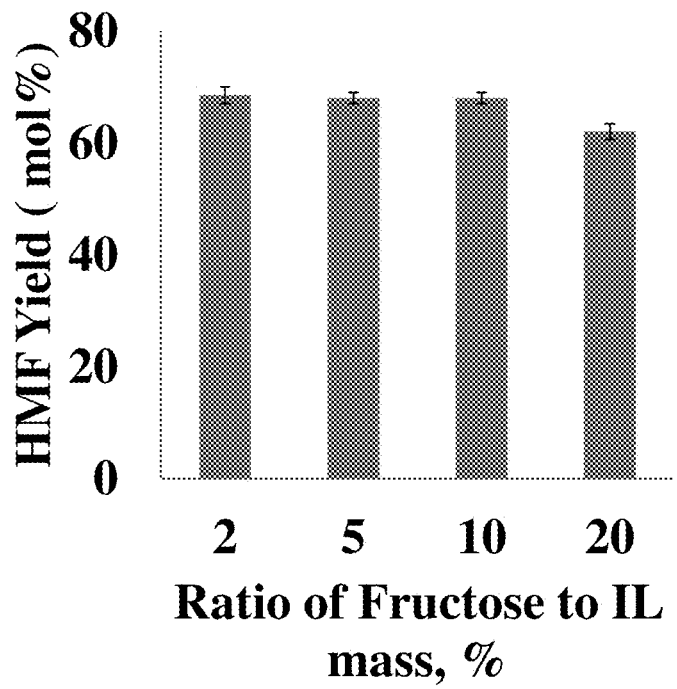
FIG. 10: Effect of fructose loading on HMF yield with simultaneous HMF extraction into THF. The dehydration was conducted at 50° C. for 180 min with fructose (20, 50, 100, or 200 mg) in 1000 mg [EMIM]$HSO_4$, a molar ratio of HCl to fructose of 0.55, and 12 ml THF for in situ HMF extraction. A slight reduction in HMF yield (68 to 62%) was observed as the mass ratio of fructose increased from 10% to 20%. Error bars are for duplicate experiments.

Effect of Fructose Loading on HMF Yield with Simultaneous HMF Extraction into THF Since the IL and HCl serve as catalysts for the dehydration reaction, the effect of fructose loading in the IL on the overall reaction yield was evaluated to determine if any reduction in yield would be seen at high sugar loadings. In these experiments, fructose (20, 50, 100, or 200 mg) was added to 1000 mg of IL with an HCl:fructose molar ratio of 0.55, and the mixture was heated to 50° C. for 180 min. The yields of HMF achieved are shown in FIG. 10. These results indicate that increasing fructose loadings up to 10% (mass ratio to IL) do not reduce the HMF yield. A slight reduction in HMF yield was seen in going from 10% to 20% (68% to 62% HMF yield). Consequently, it is possible to use an even lower volume of [EMIM]HSO$_4$ for BE to further concentrate fructose without a loss of HMF yield during the dehydration reaction.

Example 11

Reusability of the IL-HCl Phase for Fructose to HMF Conversion

Figure 11:
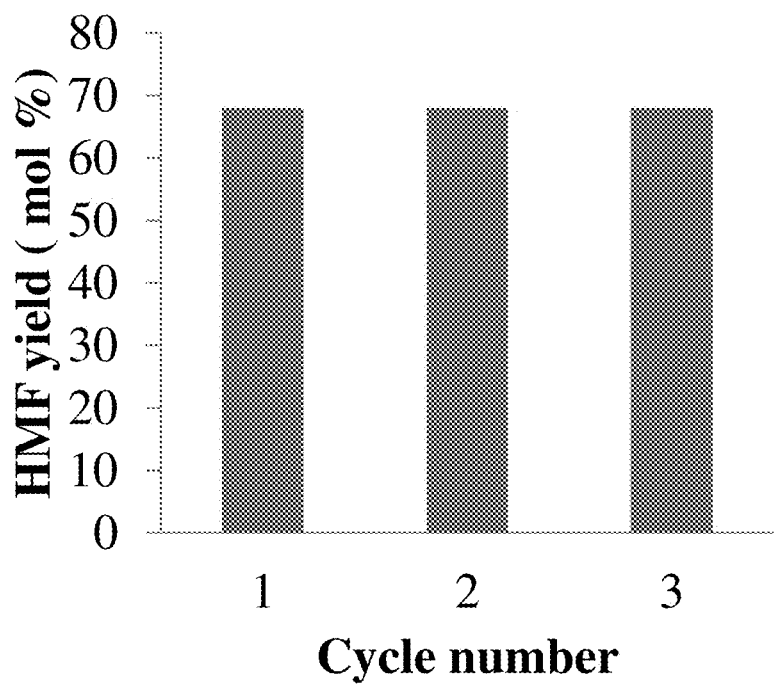
FIG. 11: Evaluation of the reusability of the ionic liquid for repeated cycles of dehydration of fructose to HMF. Data shown are the HMF yield for 3 sequential fructose dehydration runs. Dehydration media contain 1000 mg [EMIM]$HSO_4$, 100 mg fructose, 12 ml THF, and 0.42 mM HCl. Each cycle of dehydration was conducted at 50° C. for 180 min.

IL reaction media can be reused for multiple cycles of back-extraction and dehydration. Also, the conversion of glucose to HMF can be implemented in a continuous process with the IL phase as a closed loop. To measure reusability, the fructose was back-extracted into the [EMIM]HSO$_4$/HCl reaction media and the mixture was heated to 50° C. for 180 min with THF used for in situ HMF extraction. After the reaction, the THF/HMF phase was removed and the IL/HCl media was used for the second round of BE/dehydration. This process was repeated for 3 cycles with the results of the HMF yield shown in FIG. 11. Since no reduction in HMF yield was observed, these results verify the recyclability of [EMIM]HSO$_4$/HCl as a dehydration reaction media for this process.

Example 12

Side Reactions

Figure 13:
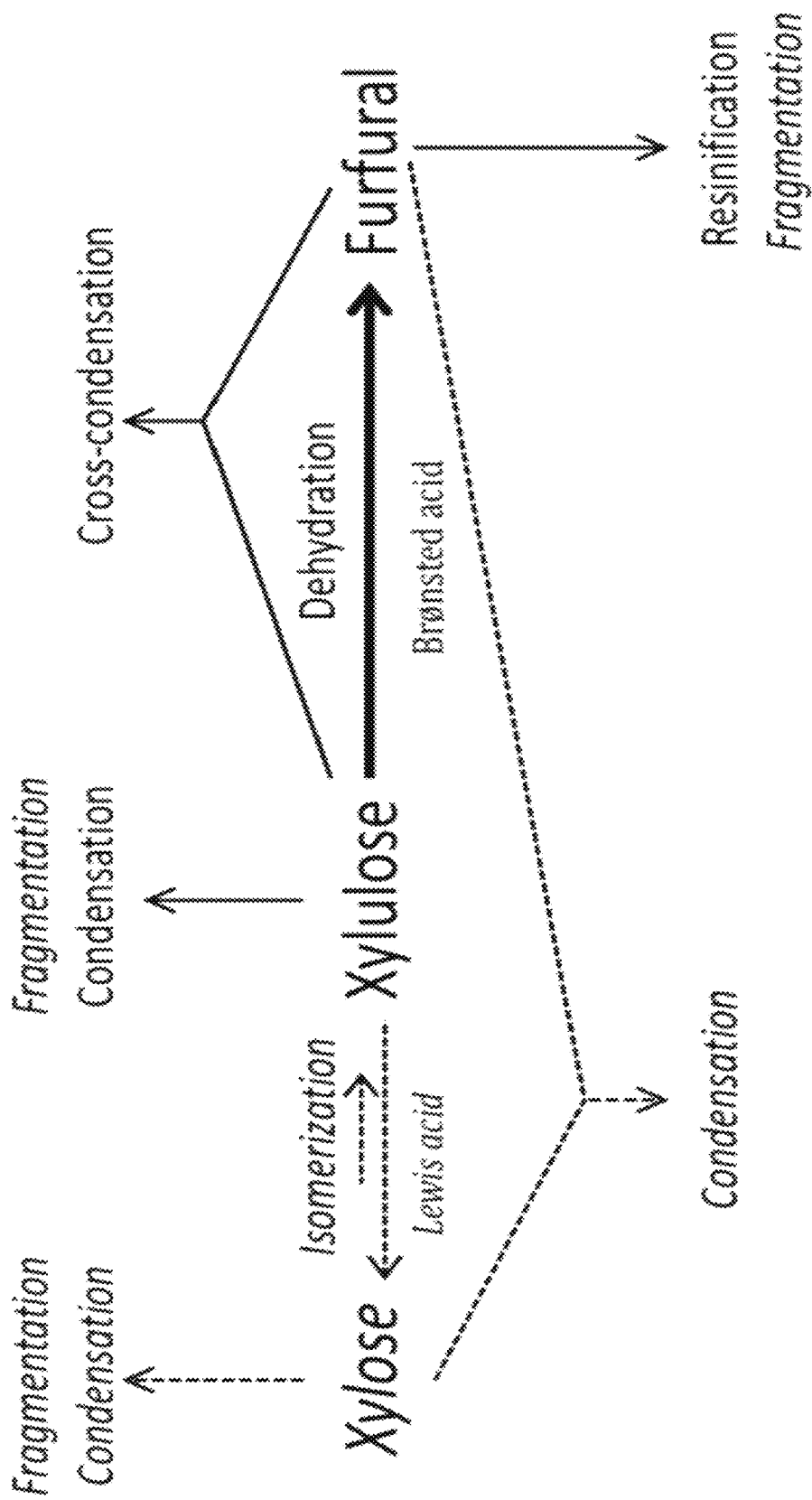
FIG. 13: Possible side-reactions of pentoses and furfural under conditions suitable for sugar dehydration. The reactants/reactions shown in italics and with dashed lines are specific to furfural production from xylose or occur only at elevated temperatures; these reactions are not present in the dehydration of xylulose. Moreover, furfural resinification is negligible under the conditions employed in the method described herein with water-DMSO media.

As FIG. 13 displays, several side-reactions of pentoses and furfural are possible under conditions suitable for sugar dehydration. Thus, by starting with ketose sugars, most of the side-reactions that plague the dehydration process in aqueous media are avoided, and high furfural yields become possible at temperatures as low as about 110° C. That even higher furfural yields (up to 90%, as seen in the examples herein) are obtained through the method described herein shows that many of the possible side-reactions are suppressed. For example, decomposition of sugars and furfural produce smaller molecules such as lactic and formic acids; however, neither were present during the dehydration of xylulose in the examples above, indicating that fragmentation of xylulose or furfural is insignificant at low temperatures. Because xylulose consumption is close to 100% in all three reaction media in the examples (water, water-DMSO, and water with solvent extraction), the very high furfural yield indicates that those side reactions specifically involving furfural may account for their relatively lower furfural yield in the water system. To confirm this, control experiments were conducted by heating furfural to 130° C. in water or water-DMSO with HCl at pH 1.

Figure 14A:
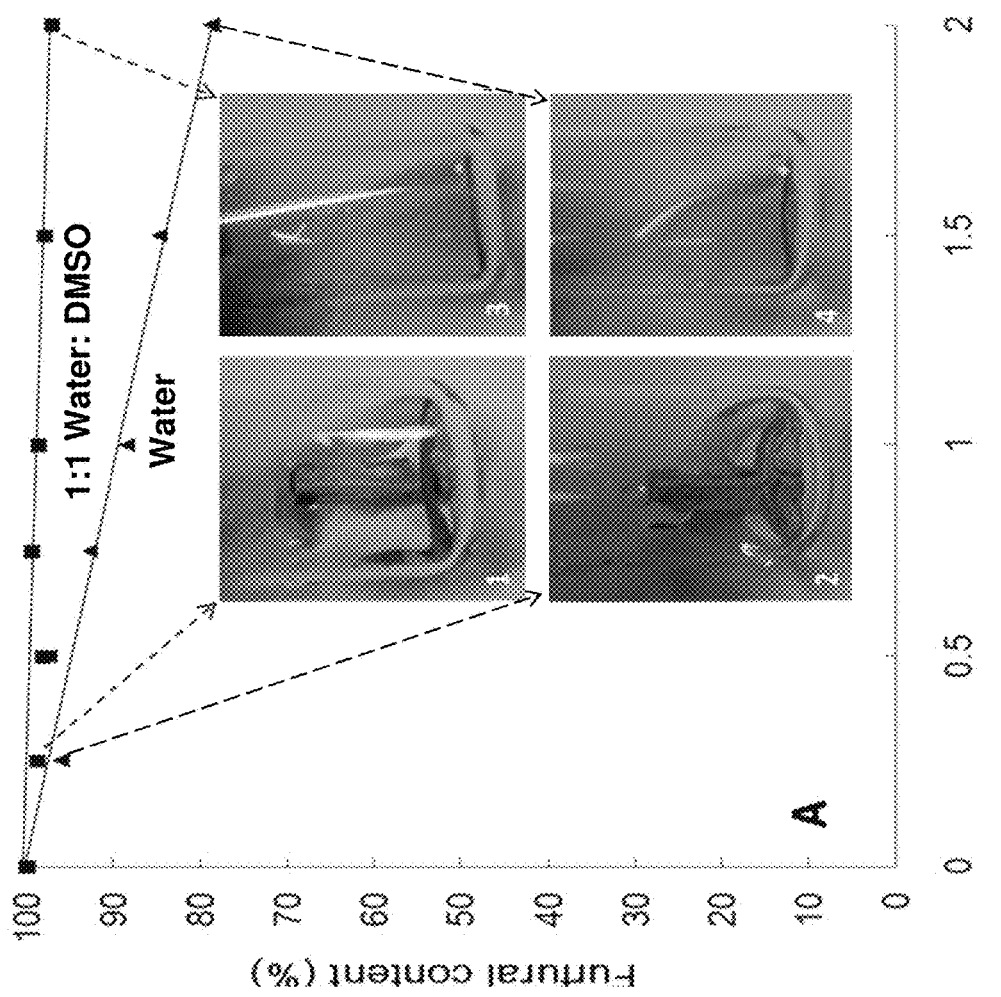
FIGS. 14A-B: Photos showing control experiments for furfural stability at 130° C. and pH 1.0.

As shown in FIG. 14A, the water-DMSO medium remained clear, indicating that furfural loss to resinification reactions in the DMSO-water system is neglible. In light of this, the small percent difference seen between xylulose consumed and furfural formed during dehydration of xylulose in the DMSO-water system can be attributed to cross-reactions between furfural and xylulose or xylulose condensation products.

Figure 14B:
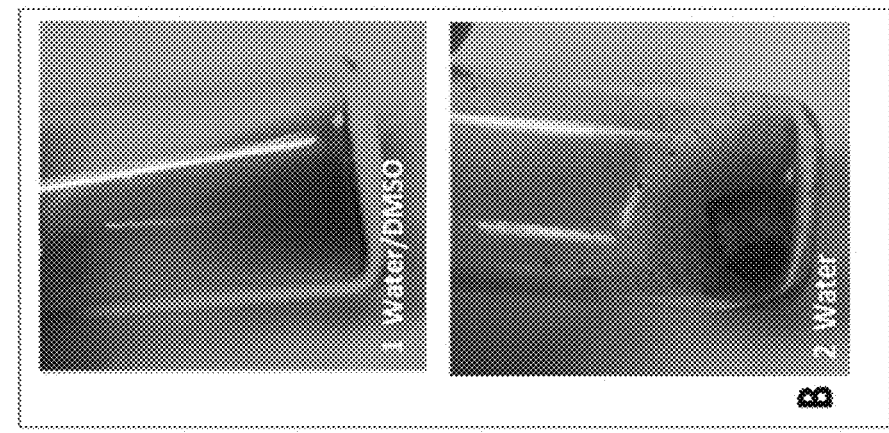

To verify how effective the method is in suppressing side-reactions at elevated sugar concentrations, a 1:1 molar ratio of furfural and xylulose was heated to 130° C. in acidic water and water-DMSO media for 15 min. Photos of the reaction media (FIG. 14B) reveal tiny, dark particulates in the water medium but no obvious formation of insolubles in the water-DMSO medium. Thus, while xylulose generates high furfural yield in aqueous media at low temperature, addition of an aprotic solvent to the media not only increases the yield further but also permits the use of much higher sugar concentrations for the dehydration.

Example 13

Figure 15:
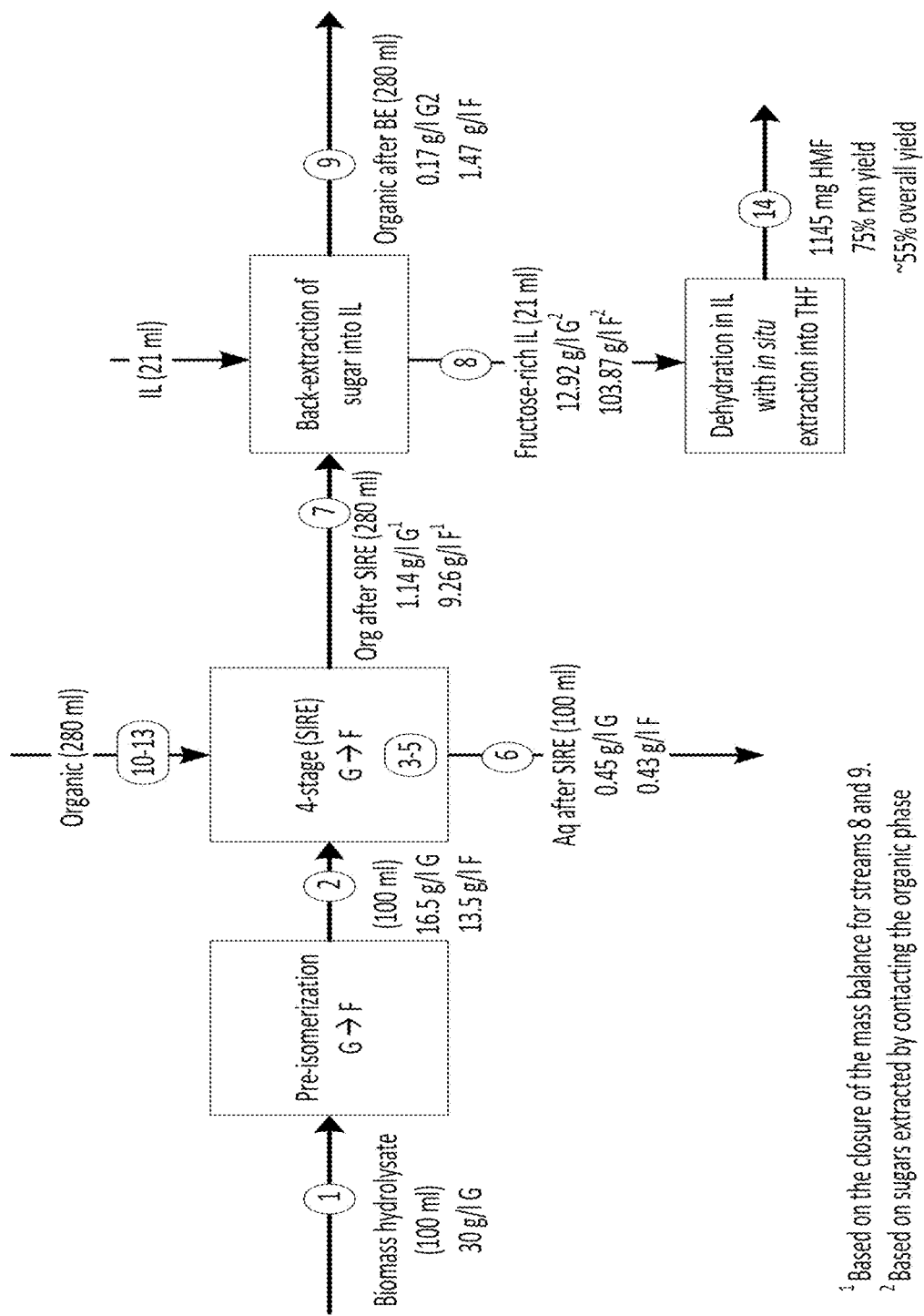
FIG. 15: Summary results for SIRE-BE-Dehydration conducted on corn stover hydrolysate prepared by dilute-acid pretreatment and diluted to a glucose concentration of 30 g/l. Conditions for SIRE-BE are the same as for those described for pure glucose SIRE-BE of FIG. 7B. Dehydration was conducted under conditions specified in Table 8, Case B3.

Efficiency of SIRE-BE-Dehydration of Glucose-rich Biomass Hydrolysate to HMF in IL Reaction Media with In Situ HMF Extraction Biomass hydrolysate produced from dilute-acid pretreatment of corn stover was diluted to 165 mM glucose to allow comparison of the SIRE-BE-Dehydration results to those of pure glucose (FIG. 7B). Experimental conditions used for SIRE were the same as described for FIG. 7B. Dehydration conditions were those described in Table 8, Case B3 using 0.42 mM HCl and 0.7 M NaCl as dehydration catalysts. Dehydration with in situ extraction of HMF into THF was conducted at 50° C. HMF yield after 180 min was 75% of theoretical yield. The results for SIRE-BE-Dehydration are summarized in FIG. 15.

Certain embodiments of the methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of producing furaldehydes from aldose sugars, comprising:
    (a) contacting an aldose sugar-containing solution with a first catalyst to form an aqueous isomerization reaction mixture comprising a ketose;
    (b) simultaneously with step (a), contacting the aqueous isomerization reaction mixture with a first immiscible phase, wherein the first immiscible phase comprises a complexing agent (CA) that binds with the ketose, to form a ketose-CA conjugate in the first immiscible phase;
    (c) maintaining the contact from step (b) at a first temperature and for a first period of time sufficient to drive aldose-ketose isomerization towards the formation of more ketose;
    (d) contacting the first immiscible phase with a second immiscible phase capable of stripping the ketose from the ketose-CA conjugate and selectively dissolving the ketose while leaving behind the CA in the first immiscible phase, wherein the second immiscible phase comprises either an ionic liquid or an aqueous HCl solution;

(e) maintaining the contact from step (d) at a second temperature and for a second period of time, with or without a second catalyst, sufficient to back-extract at least half of the ketose into the second immiscible phase; and (f) heating the second immiscible phase to a third temperature to dehydrate the ketose into a corresponding furaldehyde.

2. The method of claim 1, wherein the CA is an aryl boronic acid (ABA) selected from the group consisting of: aminophenylboronic acid, napthalene-2-boronic acid (N2B), 4-butoxy-3, 5-dimethylphenyl boronic acid, 4-tert-butyl phenyl boronic acid, and 3,5-dimethyl phenylboronic acid; and wherein the ABA is modified with one or more functional groups.

3. The method of claim 2, wherein the one or more functional groups comprises $NH_2$ or COOH incorporated into the aryl group, wherein the aryl boronic acids bind covalently bonding to a functionalized solid support.

4. The method of claim 3, wherein the functionalized solid support comprises one or more of an oxirane, an amine, an aldehyde, or a carboxyl group.

5. The method of claim 1, wherein the method further comprises sequential contact of the aqueous isomerization mixture with multiple fresh volumes of the first immiscible phase to increase aldose-to-ketose conversion and overall ketose extraction.

6. The method of claim 1, wherein the second immiscible phase comprises a hydrochloric acid solution, wherein the pH of the hydrochloric acid solution is between about 1 and about 5.

7. The method of claim 6, wherein, in step d), the second immiscible phase comprises hydrochloric acid solution with about 30 g/l of back-extracted xylulose.

8. The method of claim 6, wherein when the pH of the hydrochloric acid solution is between about 4 and about 5, less tightly complexed ketose is selectively stripped out in a first stage back-extraction that leaves behind more tightly complexed ketose in the first immiscible phase.

9. The method of claim 6, wherein when the pH of the hydrochloric acid solution is between about 1 and about 2, more tightly complexed ketose is stripped out in high purity in a second-stage back-extraction.

10. The method of claim 1, wherein the third temperature ranges from about 110° C. to about 130° C.

11. The method of claim 1, wherein the method further comprises the step of adding an aprotic solvent to facilitate dehydration of xylulose to furfural.

12. The method of claim 11, wherein the aprotic solvent comprises dimethyl sulfoxide (DMSO).

13. The method of claim 1, the method comprises multiple stages of contacting the first immiscible phase with the second immiscible phase.

14. The method of claim 1, wherein the method further comprises contacting the second immiscible phase with a third immiscible phase selected from the group consisting of: tetrahydrofuran (THF), toluene, methyl isobutyl ketone (MIBK) +2-butanol, 7:3 [v/v], MIBK, and 2-sec-butylphenol.

15. The method of claim 14, wherein the second and third immiscible phases are contacted at a 1:4 to 1:10 volume ratio.

16. The method of claim 14, wherein the second immiscible phase comprises a hydrochloric acid solution, the third immiscible phase is kept in contact with the second immiscible phase to achieve in-situ extraction of furaldehyde from the second immiscible phase as it is formed.

17. The method of claim 14, wherein the third immiscible phase consists essentially of tetrahydrofuran.

18. The method of claim 14, wherein the method further comprises the step of separating the furaldehyde from the third immiscible phase.

19. The method of claim 14, wherein the method further comprises the step of heating the third immiscible phase to a fourth temperature to evaporate the third immiscible phase and leave the furaldehyde.

20. The method of claim 19, the fourth temperature ranges from about 60° C. to about 300° C.

21. The method of claim 1, wherein the method further comprises the step of increasing the volume ratio of the isomerization mixture relative to the first immiscible phase.

22. The method of claim 1, wherein the method comprises multiple stages of back-extraction into a single volume of the second immiscible phase.

23. The method of claim 6, wherein each stage of back-extraction occurs sequentially into a single volume of the second immiscible phase.

24. The method of claim 1, wherein when present the second catalyst comprises a catalytic amount of NaBr, or NaI, a catalytic amount of the Lewis acids $AlCl_3$, $FeCl_3$, $CrCl_2$ or $CuCl_2$, or combinations thereof.

25. The method of claim 1, wherein the method comprises contacting the second immiscible phase with a third immiscible phase in proportions of 1:1, 1:2, 1:3.

26. The method of claim 14, comprising contacting the second immiscible phase comprised of aqueous HCl/furfural contacted with the third immiscible phase.

27. The method of claim 22, wherein sugars are moved from the first immiscible phase to the second immiscible phase in a two-stage back-extraction where the sugars in the first immiscible phase are split between two different second immiscible phases so as to increase the purity of the sugars in the second immiscible phase.

28. The method of claim 22, wherein sugars are extracted from multiple first immiscible phases in to a single second immiscible phase so as to increase the concentration of sugars in the second immiscible phase.

* * * * *